(12) United States Patent
Abelyan et al.

(10) Patent No.: US 8,574,656 B2
(45) Date of Patent: *Nov. 5, 2013

(54) HIGH-PURITY REBAUDIOSIDE D AND LOW-CALORIE FRUIT JUICE CONTAINING THE SAME

(75) Inventors: Varuzhan Abelyan, Kuala Lumpur (MY); Avetik Markosyan, Kuala Lumpur (MY); Lidia Abelyan, Kuala Lumpur (MY)

(73) Assignee: PureCircle Sdn Bhd, Negeri Sembilan (MY)

( * ) Notice: Subject to any disclaimer, the term of this patent is extended or adjusted under 35 U.S.C. 154(b) by 221 days.

This patent is subject to a terminal disclaimer.

(21) Appl. No.: 12/785,501

(22) Filed: May 24, 2010

(65) Prior Publication Data

US 2011/0091608 A1    Apr. 21, 2011

Related U.S. Application Data

(63) Continuation-in-part of application No. 12/580,233, filed on Oct. 15, 2009, now Pat. No. 8,299,224.

(51) Int. Cl.
    *A23L 2/00* (2006.01)
    *A23L 1/236* (2006.01)
(52) U.S. Cl.
    USPC .......................................... 426/599; 426/548
(58) Field of Classification Search
    None
    See application file for complete search history.

(56) References Cited

U.S. PATENT DOCUMENTS

| | | |
|---|---|---|
| 3,723,410 A | 3/1973 | Persinos |
| 4,082,858 A | 4/1978 | Morita et al. |
| 4,171,430 A | 10/1979 | Matsushita et al. |
| 4,361,697 A | 11/1982 | Dobberstein et al. |
| 4,599,403 A | 7/1986 | Kumar |
| 4,892,938 A | 1/1990 | Giovanetto |
| 5,112,610 A | 5/1992 | Kienle |
| 5,962,678 A | 10/1999 | Payzant et al. |
| 5,972,120 A | 10/1999 | Kutowy et al. |
| 6,031,157 A | 2/2000 | Morita et al. |
| 6,080,561 A | 6/2000 | Morita et al. |
| 2006/0083838 A1 | 4/2006 | Jackson et al. |
| 2006/0134292 A1 | 6/2006 | Abelyan et al. |

(Continued)

FOREIGN PATENT DOCUMENTS

| | | |
|---|---|---|
| CN | 101200480 A | 6/2008 |
| JP | 52005800 A | 1/1977 |

(Continued)

OTHER PUBLICATIONS

Kovylyaeva, G.I., Bakaleinik, G.A., Strobykina, I.Y., Gubskaya, V.I., Sharipova, R.R., Alfonsov, V.A., Kataev, V.E., and Tolstikov, A.G. 2007. Glycosides from *Stevia rebaudiana*. Chemistry of Natural Compounds. V.43, No. 1, 81-85.

(Continued)

*Primary Examiner* — Humera Sheikh
*Assistant Examiner* — Subbalakshmi Prakash
(74) *Attorney, Agent, or Firm* — Pyprus Pte Ltd

(57) ABSTRACT

The invention provides methods of purifying Rebaudioside D from the *Stevia rebaudiana* Bertoni plant extract along with Rebaudioside A. The methods are useful for producing high purity Rebaudioside D and Rebaudioside A. The invention further provides a low-calorie fruit juice containing the purified Rebaudioside D and a process for making the low-calorie fruit juice containing the purified Rebaudioside D.

10 Claims, 11 Drawing Sheets

| Compound name | $R_1$(C-19) | $R_2$(C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1) β-Glc(3→1) |
| 7. Rebaudioside B | H | β-Glc-β-Glc(2→1) β-Glc(3→1) |
| 8. Rebaudioside C (Dulcoside B) | β-Glc | β-Glc-α-Rha(2→1) β-Glc(3→1) |
| 9. Rebaudioside D | β-Glc-β-Glc(2→1) | β-Glc-β-Glc(2→1) β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1) β-Glc(3→1) |
| 12. Dulcoside A | β-Glc | β-Glc-α-Rha(2→1) |

(56) References Cited

U.S. PATENT DOCUMENTS

| | | | |
|---|---|---|---|
| 2006/0142555 | A1 | 6/2006 | Jonnala et al. |
| 2007/0082103 | A1 | 4/2007 | Magomet et al. |
| 2007/0292582 | A1 | 12/2007 | Prakash et al. |
| 2008/0108710 | A1* | 5/2008 | Prakash et al. ............ 426/66 |
| 2008/0226802 | A1* | 9/2008 | Lee ............................ 426/594 |
| 2008/0300402 | A1 | 12/2008 | Yang et al. |

FOREIGN PATENT DOCUMENTS

| | | | |
|---|---|---|---|
| JP | 52083731 | A | 7/1977 |
| JP | 52100500 | A | 8/1977 |
| JP | 52136200 | A | 11/1977 |
| JP | 54030199 | A | 3/1979 |
| JP | 54132599 | A | 10/1979 |
| JP | 55039731 | A | 3/1980 |
| JP | 55081567 | A | 6/1980 |
| JP | 55092400 | A | 7/1980 |
| JP | 55120770 | A | 9/1980 |
| JP | 55138372 | A | 10/1980 |
| JP | 55159770 | A | 12/1980 |
| JP | 55162953 | A | 12/1980 |
| JP | 56099768 | A | 8/1981 |
| JP | 56109568 | A | 8/1981 |
| JP | 56121453 | A | 9/1981 |
| JP | 56121454 | A | 9/1981 |
| JP | 56121455 | A | 9/1981 |
| JP | 56160962 | A | 12/1981 |
| JP | 57002656 | A | 1/1982 |
| JP | 57005663 | A | 1/1982 |
| JP | 57046998 | A | 3/1982 |
| JP | 57075992 | A | 5/1982 |
| JP | 57086264 | A | 5/1982 |
| JP | 58028246 | A | 2/1983 |
| JP | 58028247 | A | 2/1983 |
| JP | 58212759 | A | 12/1983 |
| JP | 58212760 | A | 12/1983 |
| JP | 59045848 | A | 3/1984 |
| JP | 62166861 | A | 7/1987 |
| JP | 63173531 | A | 7/1988 |
| JP | 1131191 | A | 5/1989 |
| JP | 06007108 | A | 1/1994 |
| JP | 6192283 | A | 7/1994 |
| JP | 7143860 | A | 6/1995 |
| JP | 7177862 | A | 7/1995 |
| JP | 8000211 | A | 1/1996 |
| JP | 2002262822 | A | 9/2002 |

OTHER PUBLICATIONS

Kohda, H., Kasai, R., Yamazaki, K., Murakami, K., and Tanaka, O. 1976. New sweet diterpene glucosides from *Stevia rebaudiana*. Phytochemistry. V.15, 981-983.

Starrett, A.N., Kirbi, C.W., Pocs, R., and Brendle J.E. 2002. Rebaudioside F, a diterpene glycoside from *Stevia rebaudiana*. Phytochemistry. V.59, 367-370.

Kobayashi, M., Horikawa, S., Dergandi, I.H., Ueno, J., and Mitsuhashi, H. 1977. Dulcoside A and B, New diterpene glycosides from *Stevia rebaudiana*. Phytochemistry. V/16. 1405-1408.

Shi, R., Xu, M., Shi, Z., Fan, Y., Guo, X., Liu, Y., Wang, C., and He, B. 2002. Synthesis of bifunctional polymeric adsorbent and its application in purification of *Stevia glycosides*. Reactive & Functional Polymers. V.50. 107-116.

Chen, T., Zhang, Y., Liu, X., Shi, Z., Sun, J. and He, B. 1998. Science in China. V.41. No. 4. 436-441.

Chen, T., Zhang, Y., Liu, X., Shi, Z., Sun, J. and He, B. 1999. Science in China. V.42. No. 3. 277-282.

Fuh, W-S., Chiang, B-H. 1990. Purification of steviosides by membrane and ion exchange process. Journal of Food Science. V.55. No. 5. 1454-1457.

Zhang, S.Q., Kumar, A. Kutowy, O. 2000. Membrane-based separation scheme for processing sweetener from *Stevia* leaves. Food Research International. V.33. 617-620.

Liu, Y., Yiming, C., Lining, W., and J.Jianhua. 1991. Study of stevioside preparation by membrane separation process. Desalination, V.83. 375-382.

Chen, T., Zhang, Y., Liu, X., and He, B. 1999. Studies on the adsorptive selectivity of the polar resin with carbonyl group on rebaudioside A. Acta Polymeric Scnica. No. 4. 398-403.

Moraes, E., Machado., N.R. 2001. Clarification of *Tevia rebaudiana* (Bert.) Bertoni extract by adsorption in modified zeolites. Acta Scientiarum. V.23. No. 6. 1375-1380.

Montovaneli, I.C.C., Ferretti, E.C., Simxes, M.R., and C. Silva. 2004. The effect of temperature and flow rate on the clarification of the aqueous Stevia-extract in fixed-bed column with zeolites. Brazilian Journal of Chemical Engineering. V.21. No. 3. 449-458.

Pol, J., Ostra, EV., Karasek, P., Roth, M., Benesova, K., Kotlarikova, P., and J.Caslavsky. 2007. V.388. 1847-1857.

Bandna, V.J., Singh, B., and V.K.Kaul. 2009. An efficient microwave-assisted extraction process of stevioside and rebaudioside A from *Stevia rebaudiana* (Bertoni). Phytochemical Analysis. V.20. 240-245.

Teo, C.C., Tan, S.N., Yong, J.W.H., Hew, C.S., and E.S.Ong. 2009, Validation of green-solvent extraction combined with chromatographic chemical fingerprint to evaluate quality of *Stevia rebaudiana* Bertoni. J.Sep.Sci. V.32. 613-622.

Yoda, S.K., Marques, M.O.M., Ademir J. Petenate, A.J., and M. A. Meireles. 2003. Supercritical fluid extraction from *Stevia rebaudiana* Bertoni using CO2 and CO2+ water: extraction kinetics and identification of extracted components. Journal of Food Engineering. V.57. 125-134.

\* cited by examiner

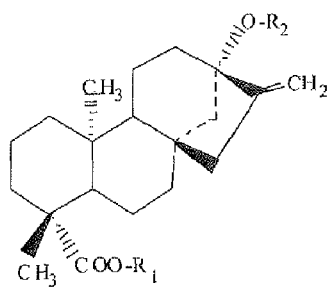

| Compound name | $R_1$(C-19) | $R_2$(C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2⇒1) |
| 5. Stevioside | β-Glc | β-Glc-β-Glc(2⇒1) |
| 6. Rebaudioside A | β-Glc | β-Glc-β-Glc(2⇒1)<br>\|<br>β-Glc(3⇒1) |
| 7. Rebaudioside B | H | β-Glc-β-Glc(2⇒1)<br>\|<br>β-Glc(3⇒1) |
| 8. Rebaudioside C (Dulcoside B) | β-Glc | β-Glc-α-Rha(2⇒1)<br>\|<br>β-Glc(3⇒1) |
| 9. Rebaudioside D | β-Glc-β-Glc(2⇒1) | β-Glc-β-Glc(2⇒1)<br>\|<br>β-Glc(3⇒1) |
| 10. Rebaudioside E | β-Glc-β-Glc(2⇒1) | β-Glc-β-Glc(2⇒1) |
| 11. Rebaudioside F | β-Glc | β-Glc-β-Xyl(2⇒1)<br>\|<br>β-Glc(3⇒1) |
| 12. Dulcoside A | β-Glc | β-Glc-α-Rha(2⇒1) |

FIG 1

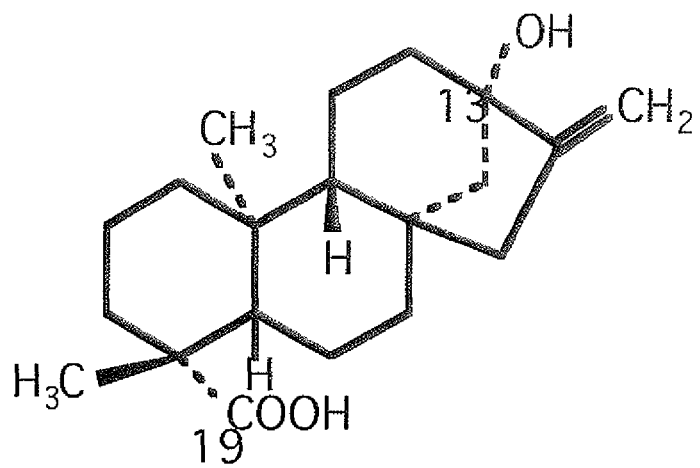
Steviol
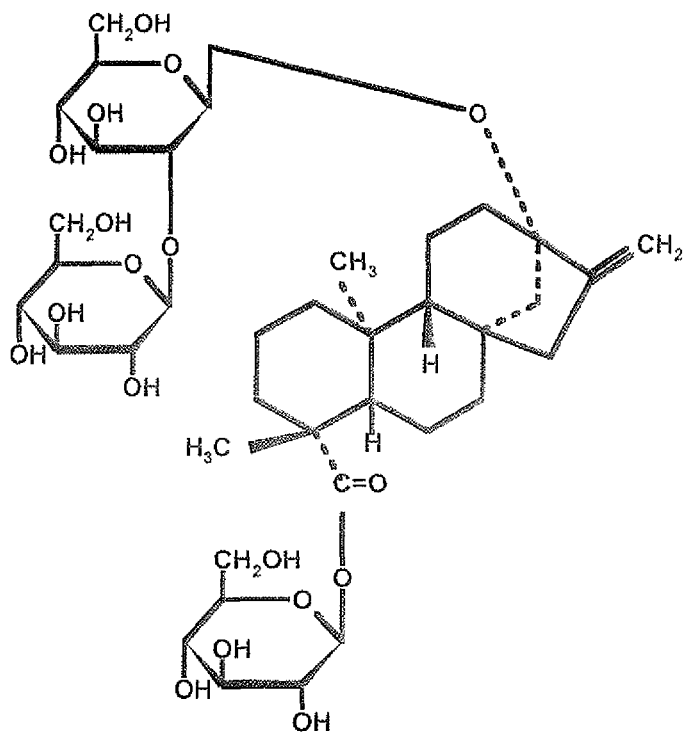
Stevioside
FIG 2

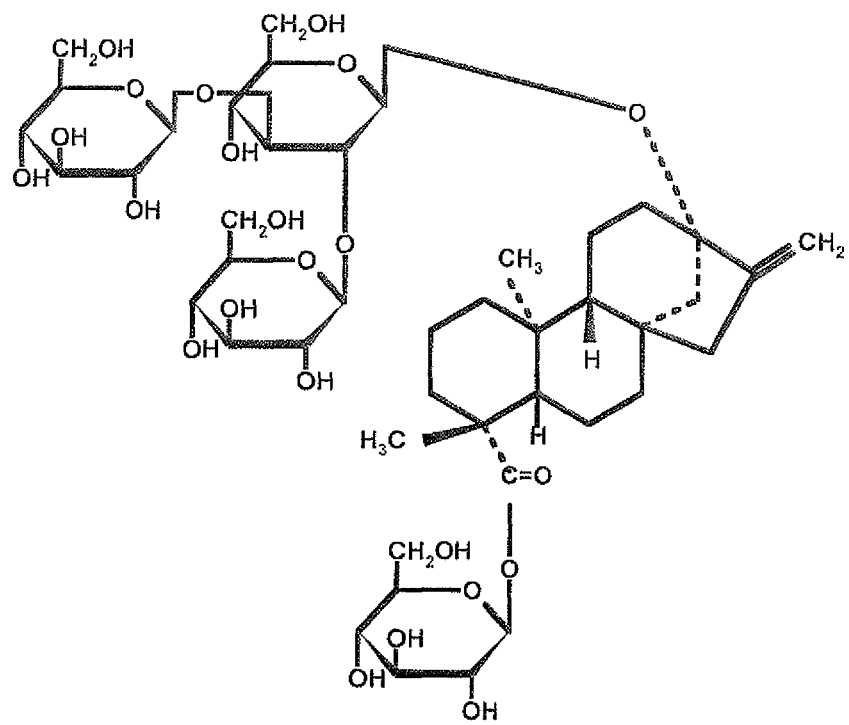
Rebaudioside A
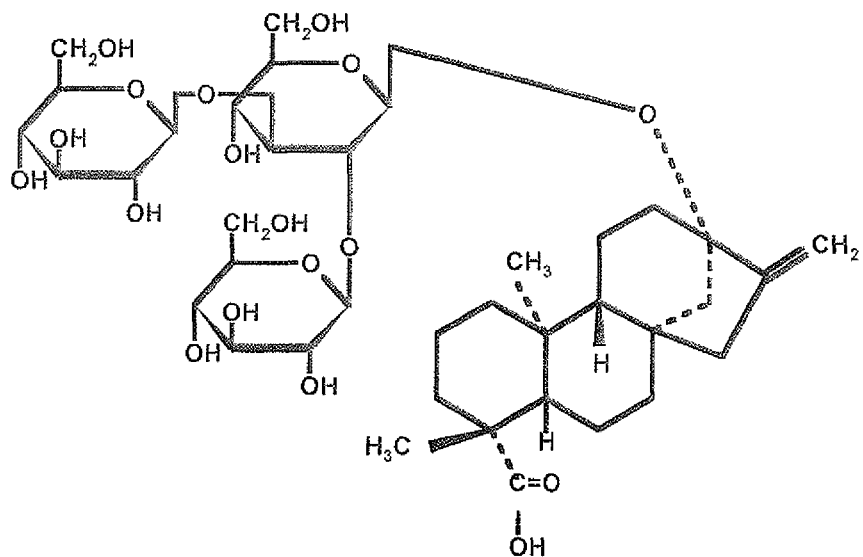
Rebaudioside B
FIG 2(Cont'd)

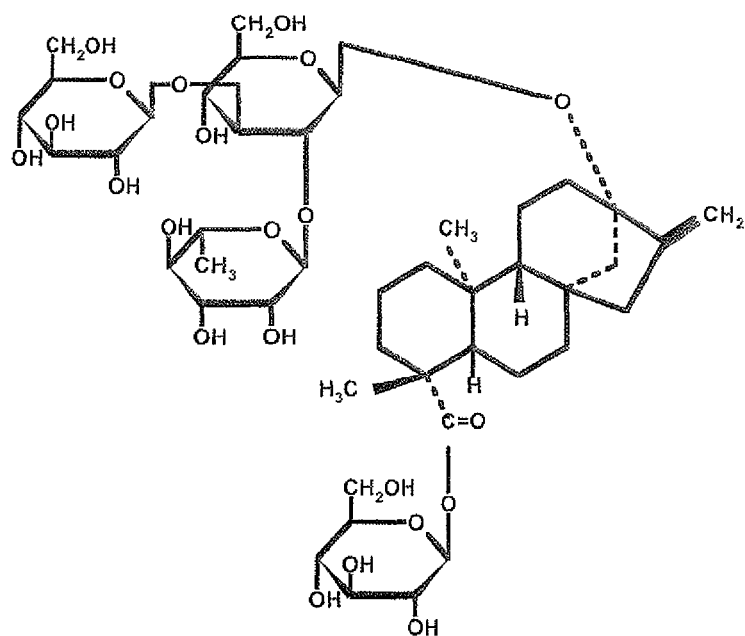
Rebaudioside C
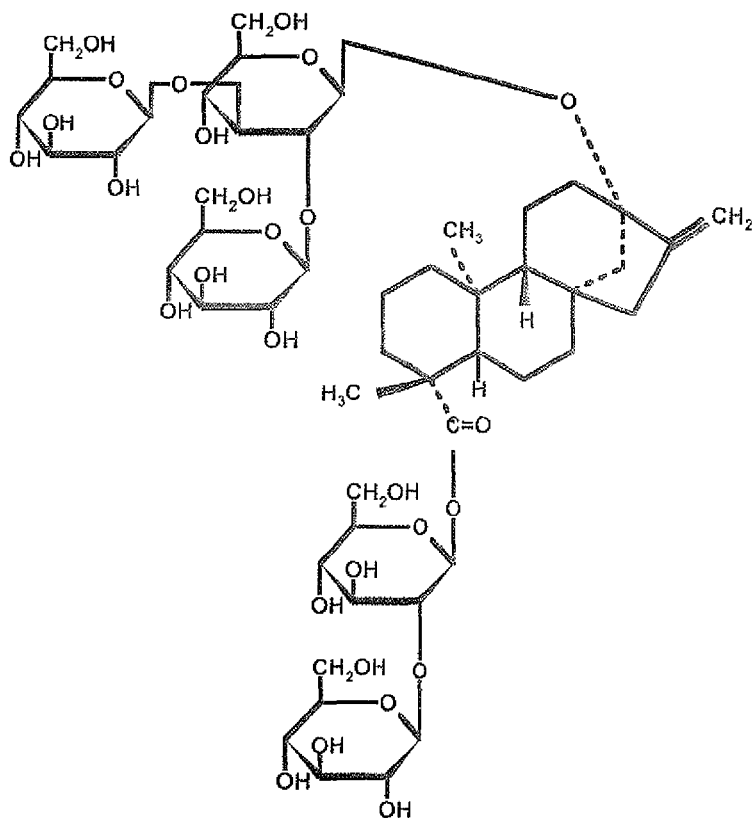
Rebaudioside D
FIG 2 (Cont'd)

Rebaudioside E

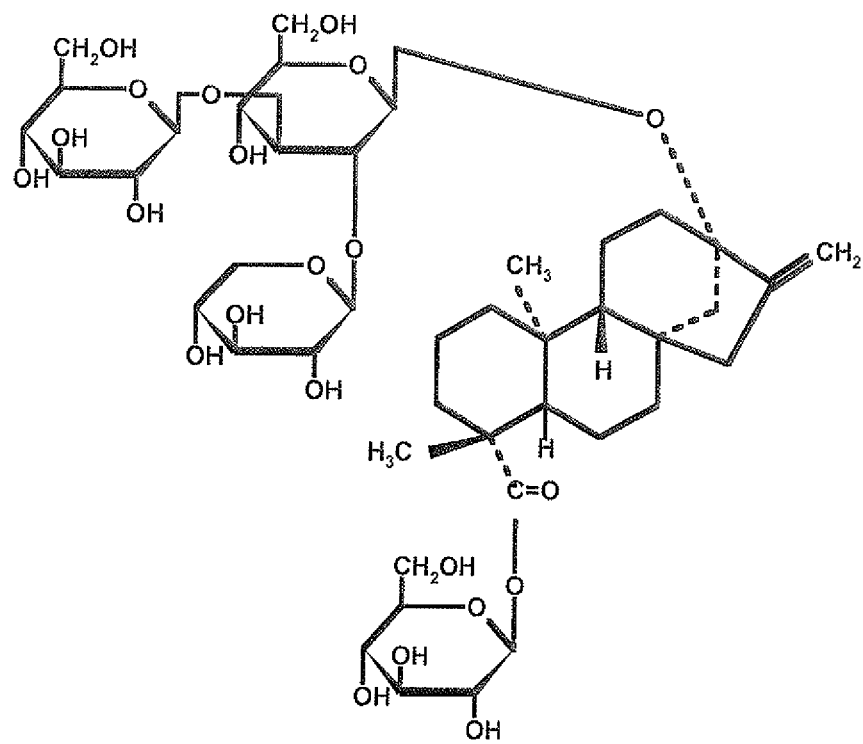
Rebaudioside F
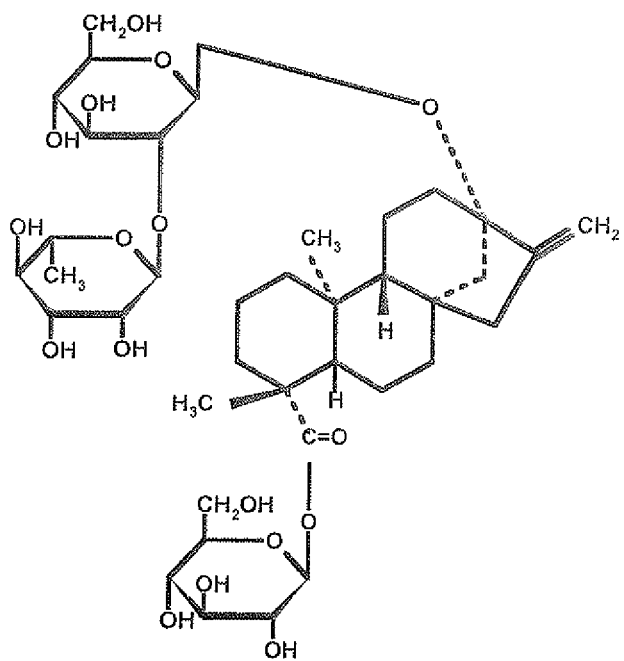
Dulcoside A
FIG 2 (Cont'd)

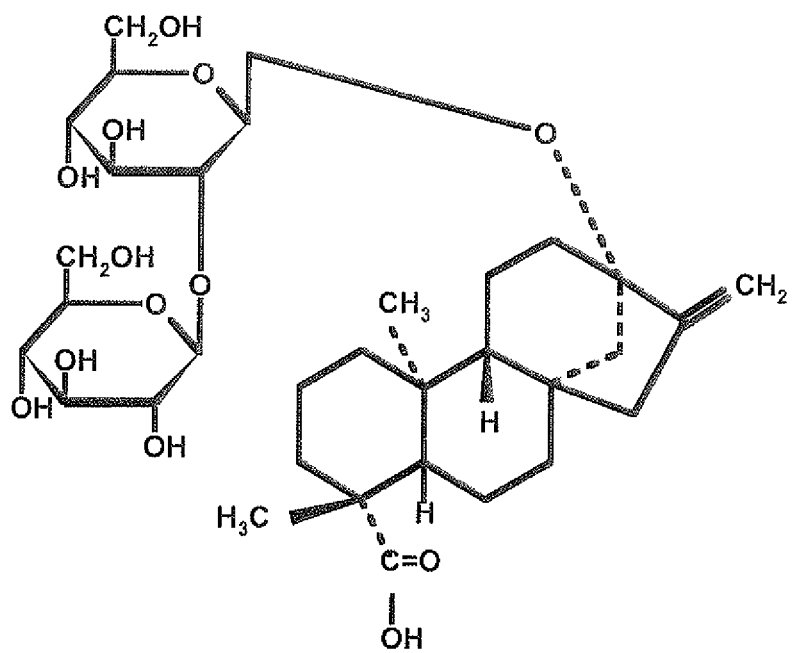
Steviolbioside
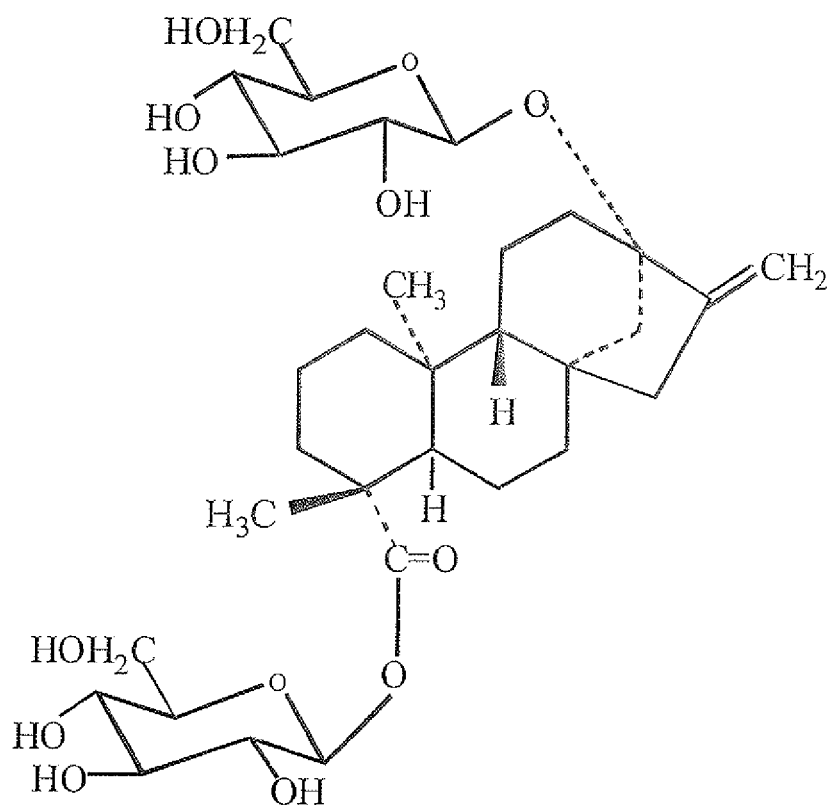
Rubusoside

HIGH-PURITY REBAUDIOSIDE D AND LOW-CALORIE FRUIT JUICE CONTAINING THE SAME

RELATED APPLICATIONS

This application is a continuation-in-part application of U.S. patent application Ser. No. 12/580,233, filed Oct. 15, 2009.

FIELD OF THE INVENTION

The invention relates to a process for isolation and purification of individual sweet glycosides from *Stevia rebaudiana* Bertoni plant extract, and more particularly to isolation and purification of Rebaudioside D from *Stevia rebaudiana* Bertoni plant extract and further to low-calorie fruit juice sweetened with high intensity sweetener.

DESCRIPTION OF THE RELATED ART

Sweeteners are critical ingredients in food supply. The demand of healthy low calorie beverages and food products results in the increasing consumption of sweeteners; thus there is a need to reduce the calories contributed by sweeteners. This goal can be achieved by using high intensity sweeteners.

High intensity sweeteners possess sweetness level many times exceeding that of sucrose. They are essentially non-caloric and used widely in manufacturing of diet and reduced calorie food. Although natural caloric sweetener such as sucrose, fructose, and glucose provide the most desirable taste to consumers, they are caloric. High intensity sweeteners do not affect the blood glucose level and provide little or no nutritive value.

However, high intensity sweeteners that generally are used as sucrose substitutes possess taste characteristics different than that of sugar, such as sweet taste with different temporal profile, maximal response, flavor profile, mouthfeel, and/or adaptation behavior than that of sugar. For example, the sweet taste of some high-potency sweeteners is slower in onset and longer in duration than that of sugar and thus changes the taste balance of a food composition. Because of these differences, usage of high-potency sweetener in replacing such a bulk sweetener as sugar in a food or beverage causes an unbalanced temporal and/or flavor profile. If the taste profile of high-potency sweeteners could be modified to impart desired taste characteristics, it can provide low calorie beverages and food products with taste characteristics more desirable for consumers.

On the other hand, high-potency sweeteners may have some cost and functional advantages compared to sugar. The competition among sugar and non-sugar high-potency sweeteners is tough in soft drinks industry, in countries where their use and production is permitted and also in countries with overvalued sugar prices.

At present high intensity sweeteners are used worldwide. They can be of both synthetic and natural origin.

Non-limiting examples of synthetic sweeteners include sucralose, potassium acesulfame, aspartame, alitame, saccharin, neohesperidin dihydrochalcone synthetic derivatives, cyclamate, neotame, dulcin, suosan, N-[N-[3-(3-hydroxy-4-methoxyphenyl)propyl]-L-α-aspartyl]-L-phenylalanine 1-methyl ester, N-[N-[3-(3-hydroxy-4-methoxyphenyl)-3-methylbutyl]-L-α-aspartyl]-L-phenylalanine 1-methyl ester, N-[N-[3-(3-methoxy-4-hydroxyphenyl)propyl]-L-α-aspartyl]-L-phenylalanine 1-methyl ester, salts thereof, and the like, and combination thereof.

Non-limiting examples of natural high intensity sweeteners include Stevioside, Rebaudioside A, Rebaudioside B, Rebaudioside C, Rebaudioside E, Rebaudioside F, Steviolbioside, Dulcoside A, Rubusoside, mogrosides, brazzein, neohesperidin dihydrochalcone (NHDC), glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, siamenoside and others.

High intensity sweeteners can be derived from the modification of natural high intensity sweeteners, for example, by fermentation, enzymatic treatment, or derivatization.

At present about eleven high intensity sweeteners are used worldwide. These are acesulfame-K, alitame, aspartame, cyclamate, glycyrrhizin, NHDC, saccharin, Stevioside, sucralose, thaumatin, neotame, and Rebaudioside A.

The high intensity sweeteners can be grouped into three generations. The first generation represented by cyclamate, glycyrrhizin and saccharin has a long history of use in food. The second generation includes acesulfame-K, aspartame, NHDC and thaumatin. Alitame, neotame, sucralose, Stevioside, and Rebaudioside A belong to the third generation.

The standard sweetening power associated with each high intensity sweetener is given in TABLE 1. However, when they are used in blends, the sweetening power can change significantly.

TABLE 1

| Sweetener | Sweetness power |
| --- | --- |
| Saccharose | 1 |
| Acesulfame-K | 200 |
| Alitame | 2000 |
| Aspartame | 200 |
| Cyclamate | 30 |
| Glycyrrhizin | 50 |
| NHDC | 1000 |
| Saccharine | 300 |
| Stevioside | 200 |
| Rebaudioside A | 450 |
| Thaumatin | 3000 |
| Sucralose | 600 |

On the other hand, 'natural' and 'organic' foods and beverages have become the "hottest area" in the food industry. The combination of consumers' desire, advances in food technology, new studies linking diet to disease and disease prevention has created an unprecedented opportunity to address public health through diet and lifestyle.

A growing number of consumers perceive the ability to control their health by enhancing their current health and/or hedging against future diseases. This creates a demand for food products with enhanced characteristics and associated health benefits, specifically a food and consumer market trend towards "whole health solutions" lifestyle. The term "natural" is highly emotive in the world of sweeteners and has been identified as one of key trust, along with "whole grains", "heart-healthy" and "low-sodium". 'Natural' term is closely related to 'healthier'.

In this respect, natural high intensity sweeteners can have better commercial potential.

New formulations of beverage products having improved nutritional characteristics, including, for example, lower calorie content, are desirable. Also, there is perceived market demand for beverages having improved flavor profiles, including good taste, mouthfeel, etc. In addition, there is consumer interest in beverages and other beverage products, such as beverage concentrates, whose formulations make greater use of natural ingredients, that is, ingredients distilled, extracted, concentrated or similarly obtained from harvested plants and other naturally occurring sources, with limited or no further processing.

The development of new beverage formulations, for example, new beverage formulations employing sweeteners, flavorants, flavor enhancing agents and the like, presents challenges in addressing associated bitterness and/or other off-tastes. In addition, such challenges typically are presented in new beverage formulations developed for improved nutritional characteristics and/or flavor profiles. Also, there is need for new beverage formulations which can satisfactorily meet the combination of objectives including nutritional, flavor, shelf life, and other objectives.

An object of the invention is to provide a beverage product having improved taste properties and mouthfeel. A beverage product comprises at least one non-nutritive sweetener in an amount sufficient to provide perceptible sweetening.

*Stevia rebaudiana* Bertoni is a perennial shrub of the Asteraceae (Compositae) family native to certain regions of South America. The leaves of the plant contain from 10 to 20% of diterpene glycosides, which are around 150 to 450 times sweeter than sugar. The leaves have been traditionally used for hundreds of years in Paraguay and Brazil to sweeten local teas and medicines.

At present there are more than 230 *Stevia* species with significant sweetening properties. The plant has been successfully grown under a wide range of conditions from its native subtropics to the cold northern latitudes.

Steviol glycosides have zero calories and can be used wherever sugar is used. They are ideal for diabetic and low calorie diets. In addition, the sweet steviol glycosides possess functional and sensory properties superior to those of many high potency sweeteners.

The extract of *Stevia rebaudiana* plant contains a mixture of different sweet diterpene glycosides, which have a single base—steviol and differ by the presence of carbohydrate residues at positions C13 and C19. These glycosides accumulate in *Stevia* leaves and compose approximately 10%-20% of the total dry weight. Typically, on a dry weight basis, the four major glycosides found in the leaves of *Stevia* are Dulcoside A (0.3%), Rebaudioside C (0.6%), Rebaudioside A (3.8%) and Stevioside (9.1%). Other glycosides identified in *Stevia* extract include Rebaudioside B, C, D, E, and F, Steviolbioside and Rubusoside (FIG. 1). Among steviol glycosides only Stevioside and Rebaudioside A are available in commercial scale.

The chemical structures of the diterpene glycosides of *Stevia rebaudiana* Bertoni are presented in FIG. 2.

The physical and sensory properties are well studied only for Stevioside and Rebaudioside A. The sweetness potency of Stevioside is around 210 times higher than sucrose, Rebaudioside A in between 200 and 400 times, and Rebaudioside C and Dulcoside A around 30 times. Rebaudioside A is considered to have most favorable sensory attributes of the four major steviol glycosides (TABLE 2).

The glycosides from leaves can be extracted using either water or organic solvent extraction. Supercritical fluid extraction and steam distillation were described as well. Methods for recovery of diterpene sweet glycosides from *Stevia rebaudiana* using membrane technology, and water or organic solvents, such as methanol and ethanol also are described.

TABLE 2

| Name | Formula | $T_{Melt}$ °C. | Mol. Weight | Optical rotation $[\alpha]^{25}_D$ ($H_2O$, 1%, w/v) | Solubility in water, % | Relative sweetness | Quality of taste |
|---|---|---|---|---|---|---|---|
| Steviol | $C_{20}H_{30}O_3$ | 212-213 | 318.45 | ND | ND | ND | Very bitter |
| Steviolmonoside | $C_{26}H_{40}O_8$ | ND | 480.58 | ND | ND | ND | ND |
| Stevioside | $C_{38}H_{60}O_{18}$ | 196-198 | 804.88 | −39.3 | 0.13 | 210 | Bitter |
| Rebaudioside A | $C_{44}H_{70}O_{23}$ | 242-244 | 967.01 | −20.8 | 0.80 | 200-400 | Less Bitter |
| Rebaudioside B | $C_{38}H_{60}O_{18}$ | 193-195 | 804.88 | −45.4 | 0.10 | 150 | Bitter |
| Rebaudioside C | $C_{44}H_{70}O_{22}$ | 215-217 | 951.01 | −29.9 | 0.21 | 30 | Bitter |
| Rebaudioside D | $C_{50}H_{80}O_{28}$ | 248-249 | 1129.15 | −29.5 (ethanol) | 1.00 | 220 | Like sucrose |
| Rebaudioside E | $C_{44}H_{70}O_{23}$ | 205-207 | 967.01 | −34.2 | 1.70 | 170 | Like sucrose |
| Rebaudioside F | $C_{43}H_{68}O_{22}$ | ND | 936.99 | −25.5 (methanol) | | ND | |
| Dulcoside A | $C_{38}H_{60}O_{17}$ | 193-195 | 788.87 | −50.2 | 0.58 | 30 | Very bitter |
| Steviolbioside | $C_{32}H_{50}O_{13}$ | 188-192 | 642.73 | −34.5 | 0.03 | 90 | Unpleasant |
| Rubusoside | $C_{32}H_{50}O_{13}$ | ND | 642.73 | 642.73 | ND | 110 | Very bitter |

There are several publications on purification of some individual steviol glycosides.

Generally production of extract includes extraction of plant material with water or water-organic solvent mixture, precipitation of high molecular weight substances, deionization, and decolorization, purification on specific macroporous polymeric adsorbents, concentration and drying.

U.S. Pat. No. 3,723,410 discloses an extraction of Steviosides from *Stevia rebaudiana* Bertoni. The method included defatting of *Stevia* leaves by treatment with chloroform for more than 150 hours at boiling temperatures and three times treatment with dioxane in the presence of calcium carbonate for two hours at boiling temperatures. After filtration the dioxane filtrates were combined and concentrated to syrup state under reduced pressure at 50° C. An equal volume of methanol was then added to the syrup and the resulting solution set aside over night to allow crystallization to occur. The crystals were collected by filtration and washed thoroughly with ice cold methanol. The residual solution was concentrated, an equal volume of methanol was added, and the mixture set aside overnight to crystallize. The crystals were removed by filtration and dried in vacuum at 100° C. The yield of Stevioside was 6.5% from air-dried leaves. The method is very complicated with the usage of toxic organic solvents. There is no information about purity of Stevioside, however in described conditions Rebaudiosides will precipitate along with Stevioside. The process is difficult to apply on commercial scale.

A method for the production of *Stevia* extract with further isolation of Rebaudioside A is developed in U.S. Pat. No. 4,082,858. The air-dried *Stevia* leaves were extracted with hot water, and the extract was dried under vacuum. The resulted mixture was extracted with methanol and from combined extracts methanol was removed by distillation under reduced pressure. The obtained syrup was subjected to chromatographic separation on a silica gel column using mixture of n-propanol, water and ethyl acetate as mobile phase. The method is useful in laboratory scale only and has various disadvantages on the commercial scale.

U.S. Pat. No. 4,171,430 discloses a purification of Stevioside from *Stevia* extract. The method included extracting *Stevia* leaves with water, concentrating the solution and extracting with methanol. Stevioside was crystallized from methanol solution and purified on styrene type gel with tetrahydrofuran as mobile phase. The method is useful in laboratory scale only. The process is difficult to apply on commercial scale.

U.S. Pat. No. 4,361,697 discloses an extraction, separation and recovery of diterpene glycosides from *Stevia rebaudiana*. The process included the steps of sequential extracting of plant material first with a solvent of intermediate polarity (such as chloroform), and then with a second solvent of high polarity (such as methanol). The resulting extract was subjected to a liquid chromatography separation. The steviol glycosides were in the methanol fraction. The major drawbacks were the use of various toxic solvents to extract and process sweet glycosides. Final purification of glycosides was achieved by column chromatography using sorbents like silica gel as a stationary phase and eluting the column with two solvents sequentially running through the column. Process is not environmentally-friendly and difficult to carry out in the large scale.

An improved method for the recovery of steviol glycosides from *Stevia rebaudiana* Bertoni plant, which does not require the use of special separation equipment such as ion exchange and/or chromatographic columns was described in U.S. Pat. No. 4,599,403. The extraction was carried out with water. The resulting aqueous extract is treated with citric acid to remove metallic and other impurities as well as to lower the pH to about 3.0. The mixture was filtered through Celite and pH of the filtrate adjusted to 10.5 by calcium oxide. The formed precipitate was remover by filtration. The filtrate was concentrated and extracted with n-butanol. Purified Stevioside crystals were then recovered by cooling the water layer obtained from the solvent extraction step. The major drawbacks of the method are the losses of glycosides during extraction by n-butanol and also low yield of Stevioside crystals from aqueous solution. The salt content in the final product can be high. There are no data about the final purity of Stevioside. The process is difficult to apply on commercial scale.

U.S. Pat. No. 4,892,938 and JP No. 01-131191 disclose a purification process in which the extract of the plant was obtained through treatment in water at a temperature from room to about 65° C. with stirring and subsequent filtration and centrifugation. This extract was treated with calcium hydroxide and the precipitate was removed by filtration or centrifugation. This filtrate was treated with a strong acidic ion exchange resin and subsequently with a weak basic ion exchange resin. The sweet glycosides remained in the water and were recovered by evaporation of the water. The disadvantage is that the final product has quite low purity. The sweet glycosides content in the final product was only about 70%.

U.S. Pat. No. 5,112,610 discloses a natural sweetener preparation process based on *Stevia rebaudiana*. The method included extracting the plant material of *Stevia rebaudiana* with an organic solvent and subjecting the solution to supercritical gas ($CO_2$) extraction to obtain a residue, which was free from undesired and taste-impairing constituents. Generally speaking, the method concerned to removal of curticle waxes, chlorophyll, other pigments and especially taste-impairing components from *Stevia* leaves or extract. However direct treatment of the leaves required a great quantity of starting material so that the use of leaves was non-economical even when increasing the bulk density of the dried or comminuted leaves by pressing into pellets prior to the extraction. The treatment of powdered extract, which was obtained from leaves by conventional method, allowed the removal of taste-impairing components only to a lesser degree, and without employing entrainers (low molecular weight alcohols, suitable hydrocarbon or mixture of the solvents) achieves not entirely satisfactory results. Moreover, there are no quantified data on the actual purity of extract. The process is difficult to apply on commercial scale.

U.S. Pat. No. 5,962,678 describes a multi-step extraction and purification process of Rebaudioside A from *Stevia rebaudiana* plant. The extract of the plant was obtained through treatment in water at a temperature ranging from ambient to about 65° C. with stirring and subsequent filtration and centrifugation. This extract was treated with calcium hydroxide and the precipitate was removed by filtration or centrifugation. This filtrate was treated with a strong acidic ion exchange resin and subsequently with a weakly basic ion exchange resin. The sweet glycosides remained in the water and were recovered by evaporation of the water. The content of steviol glycosides in the extract in this stage was 70% only. For further purification the product was passed through the column with Amberlite XAD-7, which was able to adsorb steviol glycosides. After washing with water the glycosides were desorbed with methanol. The purity of the extract was around 95% with content of significant amount of so called yellow oil. To isolate individual Stevioside and Rebaudioside A the dried solid was refluxed in anhydrous methanol solution and then cooled to precipitate Stevioside with 91.6% of purity. However, the yield of Stevioside was only 15% from the *Stevia* extract containing 60% Stevioside. Stevioside can be further purified by refluxing it in methanol-water solution. Purity of the product was about 99%.

A more purified product can be produced by the combined use of microfiltration, ultrafiltration, and nanofiltration as it is described in U.S. Pat. No. 5,972,120. The extraction was uninterruptedly carried out in continuous flow columns. The optimum mean particle size of leaves had to be about 20 mm. With smaller particles, the filtration rate substantially decreased as the column was blocked. Initial water was added in a quantity of 0.05 parts per one part of dry leaves (by weight). The column temperature was set to not more than 4° C., and extraction was carried out with water at pH within the range 2.0-4.0 (adjusted with phosphoric acid). At low temperatures and pH, a more selective extraction occurred and nearly colorless solution was obtained. The extract was then filtered through tubular ceramic membranes and, then, through ultrafiltration membranes. The produced filtrate was separated from low-molecular impurities on nanomembranes at elevated temperatures.

Method of preparation of *Stevia* extract is described in U.S. Pat. Nos. 6,031,157 and 6,080,561. The dry leaves were extracted with 10 to 20 parts of water several times. The resulting extracts were combined and passed slowly through a column filled with cation-exchange resin and then a column filled with anion-exchange resin. The treated solution then was passed through a column packed with a resin (Amberlite XAD-2) to adsorb the sweetening components, and then washed with water. After the water was drained from the column, it was eluted with three volumes of methanol to isolate the sweetening components. The effluent was concentrated and further dried under a reduced pressure to obtain a pale yellow powder. The major drawback of the method is the low quality of extract. Treatment with ion-exchangers and specific adsorbents only, cannot result in high quality *Stevia* extract with white color and high content of steviol glycosides.

U.S. Published Patent Application No 2006/0142555 discloses a process for the production of Steviosides from *Stevia rebaudiana* plant. The method included extraction of plant powder by direct steam injection into the extractor followed by filtration to get aqueous extract and calcium hydroxide treatment to remove impurities in the form of precipitate. The filtrate was treated with strong cation-exchange resin and then weak base anion-exchange resin. The aqueous eluate containing Steviosides was concentrated to obtain purified Steviosides with 45.47-65.5% Stevioside content in the final product. The provided method is suitable for production of *Stevia* extract with various content of Stevioside but not for highly purified steviol glycosides.

U.S. Patent Application Publication No. 2006/0083838 reports a method of isolating and purifying Rebaudioside A from commercially available *Stevia rebaudiana* starting material. The method comprised: (1) an EtOH formulation stage to formulate a selected EtOH solvent, (2) a first reflux stage using the *Stevia* starting material and optionally additional reflux stages using retentate isolated from a refluxed mixture or a stirred wash mixture, (3) optionally, one or more stirred wash stages, and (4) an ethanol purge and drying stage. In embodiments that used lower quality *Stevia* starting material, a second reflux stage was typically added before the stirred wash stage to maximize purity of the Rebaudioside A final product. In the reported method, an EtOH formulation stage was conducted in order to formulate a desired reflux solvent for use in the reflux step(s). Typically, the reflux solvent was a mixture of ethanol and water with about 5% to 15% by volume water. The process further included one or more energy-intensive refluxing steps that were typically conducted at a temperature of about 89° C. to 90° C. for about 1 hour. The method reportedly produced 100% pure, water-soluble Rebaudioside A.

U.S. Patent Application No. 2006/0134292 reports a process for recovering sweet glycosides from *Stevia rebaudiana* plant material. The dried and powdered leaves were treated with water in the presence of a pectinase, cellulase, and alpha-amylase. The use of such enzymes was reported to considerably increase the extraction rate and facilitates the next stages of purification. The resulting extract was purified using treatment with calcium hydroxide and ultrafiltration. Permeate was passed through the column packed with bentonite and concentrated to syrup state under vacuum. The treatment with ethanol allowed separating the practically pure Rebaudioside A from the mixture. The Rebaudioside A with high purity was obtained after washing the crystals with 88-95% of ethanol.

U.S. Patent Application No. 2007/0082103 reports a process for preparing of *Stevia* extract and highly purified Stevioside and Rebaudioside A. The dried and powdered leaves were subjected to water extraction and the resulted extract was purified using treatment with a base such as calcium hydroxide and then iron chloride. The filtrate was deionized using ion-exchange resins, concentrated under vacuum and spray dried. Highly purified Rebaudioside A and Stevioside were obtained by dissolving the extract in methanol to precipitate Stevioside. The remaining solution after isolation of Stevioside was dried and Rebaudioside A was isolated by treatment with ethanol. The final purification of Rebaudioside A was developed by treatment with ethanol-water solution. The purity was at least 98%.

U.S. Published Patent Application No 20070292582 discloses purification of Rebaudioside A. The method comprised the steps of combining crude Rebaudioside A and an aqueous organic solvent to form a Rebaudioside A solution, the aqueous organic solution comprising water in an amount from about 10% to about 25% by weight, and crystallizing from the crude Rebaudioside A solution, in a single step, substantially pure Rebaudioside A in purity greater than 95%. In the case of ethanol-methanol-water mixture the yield of Rebaudioside A with purity more than 97% was 32.5% from starting material containing 77.4% Rebaudioside A. The yield from starting material containing 80.37% Rebaudioside A was in the range of 54.6-72.0%. Other co-solvents used along with ethanol such as ethyl acetate, 1-butanol, 2-butanol, tert-butanol, sec-butanol, acetonitrile, isopropanol, and 1-propanol were not suitable for the production of Rebaudioside A with greater than 97% purity. In the case of use ethanol with various amounts of water as crystallization solvent the yield of Rebaudioside A was in the range 39.6%-76.4% from starting material containing 80.37% Rebaudioside A. The process used the mixture of two organic solvents, which recovery and purification in large scale was very complicated. Moreover, in commercial scale when centrifugation may take relatively long time, the co-precipitation of Stevioside, Rebaudioside C, and Rebaudioside D may occur.

U.S. Patent Application No. 2008/0300402 and Chinese Patent No 101200480 report a method for producing purified Rebaudioside A comprising the following steps: separation of Rebaudioside A on chromatographic column packed with silica gel using the mixture of ethyl acetate, ethanol and water as mobile phase. Rebaudioside A fractions were combined and dried. The solid was treated with ethanol containing from 2 to 10% of water and Rebaudioside A was crystallized by cooling the mixture at −20° C. The purity of Rebaudioside A can reach to more than 99%. For the purification of Rebaudioside A the filtrate after separation of Stevioside was concentrated and cooled to 0° C. overnight for about 16 hours. The resulting precipitate of Rebaudioside A was filtered, washed with a small volume of cold methanol, and dried to obtain Rebaudioside A with 79.0% purity and 3.3% yield from initial extract. This crude Rebaudioside A was further purified by refluxing in anhydrous methanol or methanol-water mixture. From starting material containing 90.2% of Rebaudioside A the output of the product was around 67% with 98.6% of purity. However the method of improving the purity of Rebaudioside A from 79% to 90.2% is not available. The major drawback of the process is low yields of the final highly products, which makes the process not suitable for commercial production of highly purified Stevioside and Rebaudioside A.

Various Japanese patents also concern about the preparation of extract from *Stevia rebaudiana* Bertoni.

JP No. 52-100500 describes the purification and concentration of aqueous Stevioside extract by treating the extract with specific ion-exchange resin of high decolorizing capacity, followed by treatment with Amberlite XAD type specific adsorbent. Treatment with only ion-exchangers and adsorption/desorption is unable to result in high quality extract.

JP No. 52-136200 discloses a preparation of Stevioside solution by extraction with hot water or hydrous alcohol followed by membrane separation. The molecular weights of sweet glycosides and sterebins are very close and membrane systems cannot result satisfactory resolution of these compounds, which will affect to the purity of extract. Content of salts in the final product will be high.

JP No. 52-005800 discloses a method of preparation of purified Stevioside from leaves of *Stevia rebaudiana* by extraction and treatment with cation-exchange resin. Such treatment will result in yellow powder with apparently low content of sweet glycosides.

Japanese Patent JP54030199 discloses the process for preparation of *Stevia* sweetening agent free from characteristic smell and bitter taste, by extracting leaves of *Stevia rebaudiana* Bertoni with water, treating the extract with a non-polar synthetic adsorbent resin followed by desorption, and further treating with an ion-exchange resin. The process is very similar to traditional Chinese technology, which allows producing *Stevia* extract with steviol glycosides content not more than 85-86%.

JP No. 54-132599 discloses a separation and purification of Stevioside by extracting *Stevia* leaves with hot water, treating the extract with a non-polar synthetic adsorbent, washing the resin with an aqueous solution of slaked lime, and eluting the Stevioside from the resin with a hydrophilic organic solvent or hydrous hydrophilic organic solvent. Treatment with only non-polar synthetic adsorbent is unable to result in high quality extract; no measures are taken for residual salts and the color of the product.

JP No. 55-159770 concerns the extraction and purification of Stevioside by extracting *Stevia* leaves with water or hydrous alcohol. The extract was concentrated to solid content from 10 to 50%, added 0.1-5.0% of calcium chloride to coagulate and precipitate the colloidal impurities existing in the extract. From concentrated solution using $CaCl_2$ most of impurities cannot be removed. There are no desalting and decolorizing stages.

JP No. 55-162953 concerns the preparation of Stevioside by extracting *Stevia* leaves with 10-15 volumes of water at 60-80° C. The extract was treated with slaked lime with aeration, and the pH of suspension was adjusted to around 8.0 by adding sulfuric or citric acid. The resulting slightly soluble salt was filtered off and the filtrate was then contacted with a polyamide resin to remove impurities. The filtrate was further extracted with n-butanol and the organic phase was distilled under the vacuum to recover the Stevioside as white crystals. Content of salts in such product will be high. Purification process using the n-butanol extraction is difficult to apply on commercial scale.

JP No. 55-081567 describes the extraction and purification of Stevioside. The extract of *Stevia* leaves prepared by water or hydrous alcohol extraction was concentrated, and one or more types of water-soluble salts of Ca, Fe, and Al and a water soluble organic solvent, e.g. ethanol or acetone, were added to the concentrate to precipitate and remove the colloidal impurities. The resulting liquid with pH 3-7 was passed through a strong cation-exchange resin and a weak anion-exchange resin. The obtained solution was passed through the specific adsorbent. The fractions of Stevioside were combined. The process is similar to the traditional Chinese technology, which can result in yellow powder with only 85-86% steviol glycosides content.

JP No. 55-120770 concerns the purification of Stevioside solution. The leaves and stalks of *Stevia rebaudiana* Bertoni were extracted with water or an alcoholic solution, to which a water-soluble tin salt, e.g., stannous chloride, stannous sulfate, stannic sulfate, etc, was added and dissolved. An alkali substance, e.g., sodium hydroxide or lime was added to the resulting solution to adjust the pH value around 5-10. The formed precipitate was separated. This process is unable to result in extract free from salts and other low-molecular weight impurities.

JP No. 55-138372 describes the purification of Stevioside solution. Stevioside was extracted from the leaves and stalks of *Stevia rebaudiana* with water, hot water, or a hydrous alcohol, and the extract or its concentrate was mixed with slaked lime or lime milk. The mixture was then filtered and mixed with an equimolar amount of water-soluble iron compound, e.g. ferrous sulfate, and stirred to precipitate the iron ions as a sparingly soluble hydroxide, which was removed with the coloring substances adsorbed on it. The process is unable to result in extract free from salts and other low-molecular weight impurities.

JP No. 55-039731 concerns the extraction of Stevioside. 1 kg of dried leaves of *Stevia rebaudiana* was extracted with 3-10 volumes of water or hydrous alcohol. The extract was concentrated to solid content of 10-50% and 0.1-5% of a metallic chloride, e.g. calcium, aluminum, or iron chloride, was added. The precipitate of impurities was removed by filtration. The subsequent purification procedures with ion-exchange resins, adsorbent, and ultrafiltration membranes can be carried out further. Most of impurities cannot be removed from concentrated solution using salts. The content of low-molecular weight impurities can be high.

JP No. 56-160962 discloses a purification of Stevioside containing solution by extracting *Stevia* leaves with water, concentrating the extract obtained to 25-50% solids content, mixing the concentrate with a low molecular weight aliphatic alcohol, and removing the precipitated impurities from the mixture. The amount of the alcohol was at least 5 times volume of the aqueous extract, or 3-6 times volume of the concentrate. The treatment is not suitable to remove low-molecular weight impurities. There are no decolorizing stages. Process is difficult to apply on commercial scale.

JP No. 56-109568 discloses a purification of *Stevia* sweetening substances by extracting *Stevia* leaves with water or hydrophilic organic solvent. The extract was treated with an organic solvent selected from the group consisting of 4-8C ether, 4-7C ester, and 1-4C organic chlorine compound, and the ingredient soluble in the solvent was separated. Diethyl ether, diisopropyl ether, ethyl acetate, methyl chloride, carbon tetrachloride, etc. may be cited as the purifying solvent. The bitter taste can be removed effectively with simultaneous decolorizing. However, used hazardous solvents, can remain in the final product. Process is difficult to apply on commercial scale.

JP No. 56-099768 concerns the preparation of steviol glycosides. A solution containing steviol glycosides, e.g. an aqueous extract of *Stevia rebaudiana* Bertoni, was treated with magnesium silicate aluminate to adsorb impurities, e.g. pigments or proteins. However, salts content in the final product can be high. There are no decolorizing and additional purification stages. Steviol glycosides content in the final product can be low.

JP No. 57-002656 concerns the discoloration and purification of *Stevia* extract. *Stevia* extract was treated with an aqueous solution of a barium compound that is readily soluble in water and then neutralized with sulfuric acid. Barium hydroxide was added until pH was 7-9 and the suspension again was treated with sulfuric acid to pH 3-4. The precipitate was separated. The main drawbacks are that salt content in the final product can be high, there are no decolorizing and additional purification stages, and, as a result, steviol glycosides content in the final product can be low.

JP No. 57-005663 concerns the purification of Stevioside through extraction. An extracted solution of *Stevia* leaves with water or water-containing alcohol was concentrated to 10-50% of solids content. A salt or a base of calcium, iron, or aluminum was added and the precipitate was removed by filtration. The filtrate pH was adjusted between 5-7, and the formed precipitate was removed. The filtrate is treated with a cation exchange and an anion exchange resins and evaporated to dryness. The major drawback of the method is the low quality of extract. The treatment with alkali and ion-exchangers only is not enough to produce the *Stevia* extract with white color and high content of steviol glycosides.

JP No. 57-046998 concerns the preparation of Stevioside. Raw leaves of *Stevia rebaudiana* were extracted with 10-20 volumes of water and the filtrate was treated with calcium hydroxide in an amount of 10-30% of the raw leaves weight. The pH of the suspension was then adjusted to 4-6 with sulfuric acid or citric acid. After filtration the extract was passed through a polyamide column to absorb glycosides and remove impurities. The purified extract was then concentrated under reduced pressure, pH adjusted to 8-9 with aqueous ammonia and extracted with n-butanol to afford crude Stevioside, which was then recrystallized from methanol. However, the content of residual salts can be high; there is no decolorizing stage; extraction with n-butanol and recrystallization from methanol is not viable commercially.

JP No. 57-075992 concerns the purification of Stevioside. The water extract of *Stevia rebaudiana* Bertoni was mixed with a flocculant (e.g. aluminum or polyaluminum chloride) to flocculate and remove the colloidal impurities, and then treated with a non-polar resin (e.g. Duolite ES-861) to adsorb the sweetening substance. The adsorbed substances were eluted with an organic solvent (e.g. methanol, acetone, etc.), and the solution was discolored and purified with activated charcoal and activated clay. Activated charcoal can absorb the Stevioside firmly from aqueous solution and the decolorizing and purification effects of activated charcoal can be promoted by the combined use with activated clay. However, hazardous solvents are used, which can present in the final product. Process is difficult to apply on commercial scale.

JP No. 57-086264 concerns the isolation of principal sweetening component of *Stevia*. Dried stalks and leaves of *Stevia* were extracted with cold water, hot water, hydrous alcohol, etc. The extract was coagulated or precipitated with an adsorbent, and the precipitate was removed by filtration or centrifugation to obtain a clear liquid containing the sweetening components. The components were adsorbed to a synthetic polymer adsorbent, purified to 80-90% purity, concentrated, dried, and dissolved in 3-8 volumes of hot methanol or hot ethanol. Stevioside and Rebaudioside A were crystallized from the solution simultaneously. After complete removing of the solvent, the mixed crystals were heated together with a 3-6 volumes of alcohol and separated into the solution part and the solid part by hot filtration. Stevioside can be obtained from the solution and the Rebaudioside A can be prepared by washing and drying the solid part. Method can result to the purified Stevioside and Rebaudioside A; however the quality of extract can be low because of the absence of deionization and decolorizing stages. The content of low-molecular weight impurities can be high.

JP No. 58-212759 and No. 58-212760 described the purification of *Stevia* sweetening substance. The leaves of *Stevia rebaudiana* Bertoni were extracted with water or an alcohol at pH 4. The extract was treated with calcium hydroxide and formed precipitate was filtered off. A water-soluble organic solvent such as methanol was added to the filtrate, and precipitate was removed. The amount of the water-soluble organic solvent was from 5% to 50% based on the filtrate. The filtrate obtained was purified by ion-exchange resins or adsorption resin. The main drawback is that hazardous solvent is used, which can present in the final product. Process is difficult to apply on commercial scale.

JP No. 58-028246 described the preparation of Stevioside. The raw leaf of *Stevia* was extracted with water, hot water or a water-alcohol mixture, and if necessary the extract was then concentrated. A mixture of calcium hydroxide with calcium chloride in an amount of 0.5-2.0 times that of the solid content in the extract were added to the extract or concentrated extract preferably while blowing gaseous carbon dioxide. The impurities were precipitated in the form of a colloidal material, which was separated by filtration. However, the extract quality can be low because of high content of salts and low-molecular weight compounds.

JP No. 58-028247 concerns the purification method of Stevioside solution. The raw leaves of *Stevia* were extracted with water, hot water or a water-alcohol mixture, and the extract was concentrated. Calcium hydroxide and a water-soluble high polymeric flocculant, e.g. polyacrylamide high polymer, in an amount of 1-2.5 times that of the solid content in the extract were added to the extract or concentrated extract to precipitate impurities, which were then filtered off. A transparent and almost colorless Stevioside solution was obtained. However, the extract quality can be low because of high content of salts and low-molecular weight compounds.

JP No. 59-045848 concerns the preparation of *Stevia* sweetener with high content of Rebaudioside A. Dried leaves of *Stevia* variety containing 1.57 times more Rebaudioside A than Stevioside were extracted with water or a water-containing solvent. The prepared extracted solution was treated with a cation-exchange resin and an anion-exchange resin. The solution was adsorbed on an absorption resin, eluted with a hydrophilic solvent, and the solution was concentrated to yield a natural sweetener. The process is similar to the traditional Chinese technology, which can result to the yellow powder with steviol glycosides content up to 85-86% only.

JP No. 62-166861 concerns the extraction and purification of sweetener component from dry leaves of *Stevia*. Dried leaves of *Stevia rebaudiana* Bertoni were extracted with 7-14 volumes of water at 50-70° C. for 3-6 hr with agitation to obtain a brown liquid extract with total solids content of 2-3% and containing 0.7-0.8% of Stevioside. The extract was concentrated 7-8 times at about 60° C. under reduced pressure. The concentrated liquid was treated with 0.5-2% $CaCl_2$ to separate impurities as flocculent precipitate. The solution was treated with an Al, Mg oxide of an amount corresponding to 15-20% of the solid content at 40-55° C. under vigorous agitation. Then the precipitate was removed by filtration. The Stevioside can be further purified on specific adsorbents. However, the process is difficult to commercialize; salts quantity used for the purification of extract is high and there are no deionization and decolorizing stages. The content of low-molecular weight compounds can be high.

JP No. 06-007108 concerns the method for extracting and separating sweet substances of *Stevia rebaudiana* Bertoni. Leaves of *Stevia rebaudiana* Bertoni were extracted with a water-miscible alcohol such as methanol. The extracted solution was mixed with water and passed through an ultrafiltration membranes having 20-150 kDa cutting capacity and then through the ultrafiltration membranes with 1-10 kDa cutting capacity. However, hazardous solvents are used, which can present in the final product. Process is difficult to apply on commercial scale.

JP No. 52083731 deals on isolation and purification of Rebaudioside A and Rebaudioside B by column chromatography on silica gel. Further purification is developed by crystallization from organic solvents such as methanol or ethanol.

JP No. 55-092400 concerns the preparation of Stevioside. An aqueous solution containing Stevioside was extracted with 1H, 1H, 5H-octafluoro-1-pentanol. After separating the solvent was distilled off, and the residue was dried. The precipitate was recrystallized from methanol. The purity of Stevioside was more than 95%.

JP No. 56-121453, JP No. 56-121454, and JP No. 56-121455 concern the separation of Stevioside and Rebaudioside A. A mixture of Stevioside and Rebaudioside A extracted from the leaves of *Stevia rebaudiana* Bertoni was mixed with 75% aqueous solution of methanol and maintained at ambient temperature for about 3 hours. The resulted crystals with 65% Stevioside and 25.2% Rebaudioside A content were separated by filtration and dried. In the case of application of 90% aqueous solution of ethanol the final mixture contains 57.4% Stevioside and 31.9% Rebaudioside A. Further re-crystallization from 90% aqueous solution of ethanol resulted in product with higher content of Rebaudioside A. The purity of the product was around 80%. Stevioside further can be purified up to 86.1% by additional washing with water. β-Type crystals of Stevioside and α-type crystals of Rebaudioside A were obtained.

JP No. 57-046998 concerns the preparation of Stevioside. Raw leaves of *Stevia rebaudiana* were extracted with 10-20 volumes of water and the filtrate was treated with calcium hydroxide in an amount of 10-30% of the raw leaves weight. The pH of the suspension was then adjusted to 4-6 with sulfuric acid or citric acid. After filtration the extract was passed through a polyimide column to adsorb glycosides and remove impurities. The purified extract was then concentrated under reduced pressure, pH adjusted to 8-9 with aqueous ammonia and extracted with n-butanol to afford crude Stevioside, which was then recrystallized from methanol.

JP No. 57-086264 concerns the isolation of principal sweetening component of *Stevia*. Dried stalks and leaves of *Stevia* were extracted with cold water, hot water, hydrous alcohol, etc. The extract was coagulated or precipitated with an adsorbent, and the precipitate was removed by filtration or centrifugation to obtain a clear liquid containing the sweetening components. The components were adsorbed on a synthetic polymer adsorbent, purified to 80-90% purity, concentrated, dried, and dissolved in 3-8 volumes of hot methanol or hot ethanol. Stevioside and Rebaudioside A were crystallized from the solution simultaneously. After complete removal of the solvent, the mixed crystals were heated together with a 3-6 volumes of alcohol and the solids were separated from solution by hot filtration. Stevioside can be obtained from the solution and the Rebaudioside A can be prepared by washing and drying the solid part.

JP No. 06-192283 and JP No. 08-000214 discloses purification of Rebaudioside A by gel-filtration on Toyo Peri HW-40. Rebaudioside C and Dulcoside were obtained by HPLC. Method is useful only in laboratory scale.

JP 63173531 describes a method of extracting sweet glycosides from the *Stevia rebaudiana* plant. The first step of the process was to extract a liquid solution of sweet glycosides from the *Stevia rebaudiana* plant. Secondly, the liquid solution of sweet glycosides was passed through a non-polar porous resin and eluted with a water-soluble organic solvent, preferably methanol. Thirdly, the eluted solution was concentrated and dried to give a powdery material. This procedure isolates a mixture of sweet glycosides, but does not isolate a single pure sweet glycoside such as Rebaudioside A.

JP No. 07-143860 discloses purification of Rebaudioside A through crystallization and re-crystallization from 10-20% of aqueous methanol solution. The purity of Rebaudioside A was around 90%.

JP No. 07-177862 discloses purification of Rebaudioside A and Stevioside. Purified *Stevia* extract was treated with low concentrations of alcohol to obtain crystals with about 75% content of Stevioside and Rebaudioside A. The crystals were further recrystallized from water to provide the slightly water-soluble sweetener with ratio of Stevioside and Rebaudioside A around 1:2, w/w.

JP No. 2002,262,822 discloses a sweetener extracted from dried leaves of *Stevia* plant and its extraction method. This process used water or aqueous solvent to extract *Stevia* glycosides from the dried leaves. In the obtained product, the content of Rebaudioside A is 2.56 times the amount of Stevioside.

Isolation of Steviolbioside, Rebaudioside A, Rebaidioside B was carried out by Kohda et al., 1976. Dried leaves were extracted with hot methanol and filtrate was concentrated to dryness. The residue was extracted with n-butanol and, after drying the residue was re-crystallized from methanol. The mother liquor was subjected to chromatographic separation on silica gel using chloroform-methanol-water mixture as mobile phase. Further purification was developed by thin-layer chromatography. The method can be applied only in laboratory scale for the production of small amounts of abovementioned sweet glycosides.

Dulcoside A and B were isolated and identified using crystallization from methanol-ethanol mixture and further purified by chromatography on silica gel (Kobayashi et al., 1977).

The combination of ultrafiltration, diafiltration, reverse osmosis and ion exchange treatment was used for the purification of *Stevia* extract (Fuh and Chiang, 1990). The cutting capacity of ultrafiltration membranes was 25,000 and 100,000 Daltons. The mixtures of strong and weak cation- and anion-exchange resins were used as ion-exchangers. The recovery of total steviol glycosides was around 90%; however the final product purity was 46% only.

A method for the purification of steviol glycosides by membrane technology is described by Liu et al. (1991) and Zhang et al. (2000). Dried leaves were placed in a standard glass column and extraction was carried out with reverse osmosis water. The extract was pretreated with a ceramic tubular membrane and then with an ultrafiltration membrane in diafiltration mode. Permeate was washed from lower molecular weight impurities by a nanofiltration membrane in a diafiltration mode at elevated temperatures. Addition of lime and/or other flocculating agent to ultrafiltration feed improved the flux significantly. The process could provide a relatively high purity sweetener concentrate. However there are no data about the purity of the extract and the recovery of steviol glycosides. The low pH values used for the extraction required special acid resistant reactors. Low temperatures during extraction increased the operational cost of the production. These both (low temperatures and pH) resulted in large amount of diluted initial extract. Dilution of extract occurred also during microfiltration and ultrafiltration. For the final purification ion-exchange treatment is necessary.

These factors are substantially increasing the production cost and decreasing the yield of final product in unit of time. Initial investment is high as well.

A series of polar resins based on polystyrene with carbonyl groups were used for the adsorption of steviol glycosides and partial separation of Stevioside and Rebaudioside A (Chen et al., 1998; 1999). The ratio of Rebaudioside A to Stevioside can increase from 0.72 to 2.24.

The adsorptive capacity and selectivity of a novel adsorbent with pyridyl group toward steviol glycosides were studied (Chen et al., 1999). The effect of polarity and physical structure of the sorbent on the selectivity was investigated in detail. Two separation methods were applied in the enrichment of Rebaudioside A. They were selective elution using methanol or ethanol solution as solvent, and dynamic chromatographic separation using pyridyl resin with high selectivity. Results show that the chromatographic separation method can effectively enrich Rebaudioside A from Stevia extract with high content of Stevioside. The ratio of Rebaudioside to Stevioside can increase from 0.75 to 3.94. Further purification of Rebaudioside A was possible by crystallization from methanol.

A method for clarification of Stevia extract using modified zeolites is described by Moraes et al. (2001) and Montovaneli et al. (2004). Synthetic or natural zeolites were modified by treatment with calcium or barium ions and Stevia extract without any pretreatment was contacted with modified zeolite. It resulted in 70-80% of clarification in batch and only 55-60% in continuous conditions. The clarification process was meant to adsorb the pigments that make the extract brownish, and not the glycosides, which are responsible for the sweet taste. However, there are no data on the steviol glycosides content in the final product. Obviously only this type of treatment cannot result in highly purified extract, especially because of polysaccharides, heavy metals and sterebins, which remain in clarified extract. Moreover, no data about half-life and adsorption capacity of the carrier which is very important when process is carried out in continuous conditions.

Polymeric adsorbents with —$N^+(CH_3)_3$ groups were designed and applied for the purification of steviol glycosides and enrichment of Rebaudioside A (Shi et al., 2002). In the series of five columns the content of Rebaudioside A increased from the first column product to the fifth column product. At the same time the adsorbent displayed decolorization ability.

Rebaudioside F was isolated by liquid chromatography on 3-aminopropyl-functionalized silica gel by Starratt et al., 2002. The fractions which were rich in Rebaudioside C and Rebaudioside F were combined and separated by HPLC on a Waters carbohydrate column with linear gradient of acetonitrile and water.

Preparation of Stevia extract by supercritical fluid extraction is described by Yoda et al. 2003. It is a two-step process: (i) $CO_2$ extraction at 200 bar and 30° C., and (ii) $CO_2$+water extraction. Approximately 72% of the $CO_2$-soluble compounds were recovered and the major compound was austroinulin. The system Stevia+$CO_2$+water was able to remove approximately 50% of the original Stevioside and about 72% of Rebaudioside A. The main drawbacks of the method are the requirement of high pressure and low extraction rate of sweet compounds. Besides, there is no information about content of minor compounds and total steviol glycosides content in the final extract. The process is difficult to apply on commercial scale.

Pressurized fluid extraction using water or methanol was employed for the extraction of Stevioside from Stevia rebaudiana Bertoni (Poi et al. (2007). A temperature of 110° C. was determined to be optimal for extraction of Stevioside from Stevia rebaudiana leaves using either water or methanol. An increased temperature resulted in significant degradation of Stevioside in the media of both solvents or in a decline in the extraction yield in water. Both solvents demonstrated Stevioside extraction with very similar reproducibility and the proposed extraction parameters are the same for both methods. Water represents a more environmentally conscious and cheaper alternative to methanol.

A method of preparation and purification of Stevia extract is described by Kovylyaeva et al., 2007. The method included extraction of dry leaves with 14 volumes of distilled water for 1 hrs at boiling temperatures, filtration and concentration of filtrate up to syrup state. Syrup was diluted, added $AlCl_3.6H_2O$ and stirred until it dissolved. The mixture was stirred and treated with a water solution of NaOH. The precipitate was filtered and the filtrate was passed through a column packed with $Al_2O_3$. The column was eluted with distilled water to obtain a light brown solution. Further purification of Stevioside, Rebaudioside A, and Rebaudioside C was done by extraction with n-butanol and column chromatography on $Al_2O_3$ and silica gel. The method is unable to result in high purity Stevia extract. Large amount of salts are used for the pretreatment. Purification process is difficult to apply on commercial scale.

An efficient microwave-assisted extraction process of Stevioside and Rebaudioside A is described by Bandna et al. (2009). Dried and powdered leaves of S. rebaudiana were extracted by conventional, ultrasound and microwave-assisted extraction techniques using methanol, ethanol and water as single solvents as well as in binary mixtures. Conventional cold extraction was performed at 25° C. for 12 h while ultrasound extraction was carried out at temperature of 35±5° C. for 30 min. Microwave-assisted extraction was carried out at a power level of 80 W for 1 min at 50° C. As a result microwave-assisted extraction yielded 8.64% and 2.34% of Stevioside and Rebaudioside A, respectively, while conventional and ultrasound techniques yielded 6.54 and 1.20%, and 4.20 and 1.98% of Stevioside and Rebaudioside-A, respectively.

The efficient isolation of steviol glycosides was achieved also using pressurized hot water extraction (Teo et al., 2009).

All the existing methods deal with isolation and purification of one or other steviol glycoside from the initial extract and do not show a way for the further treatment of residual solution or purification of minor compounds. Thus, there is a need for efficient and economical method for comprehensive retreatment of extract produced from Stevia rebaudiana Bertoni plant.

However, there is no published data on the commercial isolation and purification of Rebaudioside D which possess excellent sensory properties.

Rebaudioside D content in the extract is very low and because of that its purification is very difficult.

Accordingly, there is a need for a simple, efficient, and economical method for production of high purity Rebaudioside D, which can be used as sweetener in food, beverage, pharmaceutical, cosmetic, and other industries.

SUMMARY OF THE INVENTION

The invention relates to a process for isolation and purification of individual sweet glycosides from Stevia rebaudiana Bertoni plant, and more particularly for isolation and purification of Rebaudioside D and its application in low-calorie fruit juice.

The primary technical problem to be solved and the primary object of the invention are to provide a highly efficient method of isolating and purifying different steviol glycosides particularly Rebaudioside D from *Stevia* extract.

The present invention provides a process for retreatment of *Stevia rebaudiana* Bertoni plant extract with isolation and purification of highly purified individual sweet glycosides, particularly Rebaudioside D.

The highly purified Rebaudioside D alone or in the combination with other sweeteners and/or other ingredients is useful as non-caloric sweetener in edible and chewable compositions such as any beverages, confectionaries, bakeries, cookies, chewing gums, and alike.

According to the present invention the isolation and purification of Rebaudioside D was developed from *Stevia* extract. In one embodiment, the method for isolation and purification of Rebaudioside D comprises treating *Stevia* extract with a first alcohol or alcohol-water solution to form a first mixture, obtaining a first precipitate containing Rebaudioside A and Rebaudioside D from the first mixture, treating the first precipitate with a second alcohol or alcohol-water solution to form a second mixture, obtaining from the second mixture a second precipitate containing highly purified Rebaudioside A and a filtrate with high Rebaudioside D content, where the second precipitate is dried to produce high purity Rebaudioside A, and where the filtrate is concentrated to produce high purity Rebaudioside D. Optionally, the method further comprises treating the purified Rebaudioside D with a third alcohol or alcohol-water solution to refine the high purity Rebaudioside D.

An another object of the invention is to provide beverage products having improved taste properties and mouthfeel using rebaudioside D as a non-nutritive natural sweetener in an amount sufficient to provide perceptible sweetening.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 1 shows the chemical structure of steviol and the steviol glycosides present in the *Stevia rebaudiana* Bertoni leaves.

DETAILED DESCRIPTION OF THE INVENTION

The present invention provides a process for isolation and purification of individual sweet glycosides from *Stevia rebaudiana* Bertoni plant extract, and more particularly for isolation and purification of Rebaudioside D from *Stevia rebaudiana* Bertoni plant extract and its application in low-calorie fruit juice.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Among sweet glycosides existing in *Stevia* only Stevioside and Rebaudioside A are available at moderate cost at <80% purity and at high cost at >80% purity. The highest purity of commercial product usually is more than 97%. In the market there are no commercial quantities for Rebaudioside B, Rebaudioside D, and Rebaudioside C. Rebaudiosides E and F analytical standards in minor quantities are still unavailable.

Figure 2:
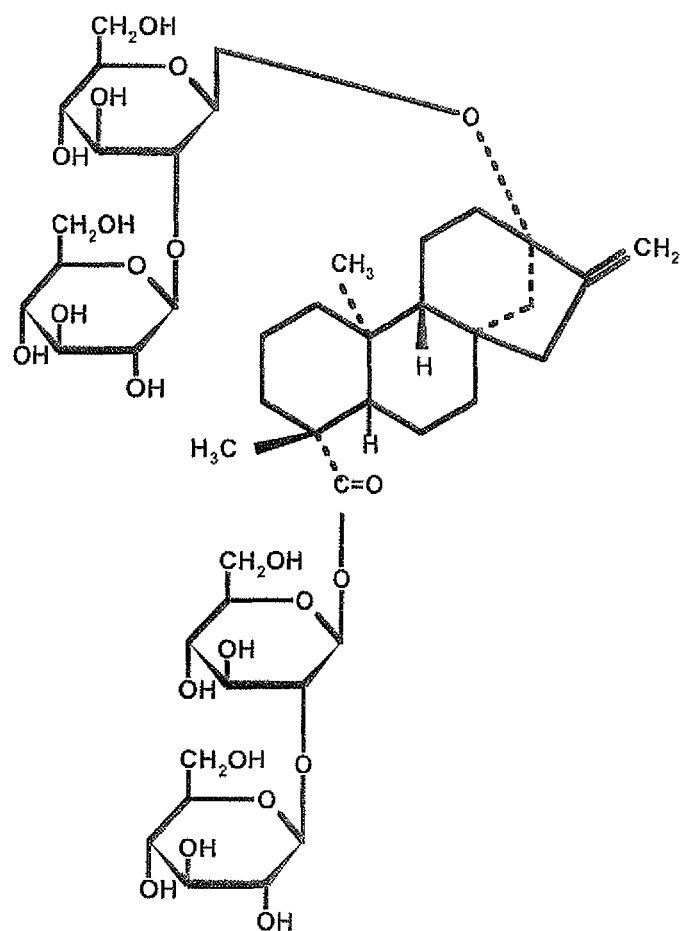
FIG. 2 shows the chemical structures of steviol glycosides present in *Stevia rebaudiana* Bertoni.

Rebaudioside D is a high-potency diterpenoid glycoside sweetener having the chemical structure presented in FIG. 2.

Rebaudioside D is isolated and extracted, along with other steviol glycosides, from the *Stevia rebaudiana* Bertoni plant ("*Stevia*"), which is commercially cultivated in Japan, Taiwan, Malaysia, South Korea, China, Israel, India, Brazil, Australia, and Paraguay. It is an ideal non-caloric sweetener with functional and sensory properties superior to those of many high-potency sweeteners. Processed forms of *Stevia* can be 30 to 400 times more potent than sugar. Amongst the sweet diterpenoid glycosides of *Stevia*, Rebaudioside D is the least bitter, and with the least persistent aftertaste.

At present there is no published commercial technology related to the isolation and purification of Rebaudioside D, and certainly there is a need for efficient and economical method for comprehensive isolation and purification of individual sweet glycosides from *Stevia* extract.

The present invention provides a method for production of highly purified Rebaudioside D from *Stevia* extract.

Hereinafter, the term "highly purified" refers to a Rebaudioside D composition that includes at least about 91% to 100% of the Rebaudioside D on dry weight basis.

Exemplary embodiments of this invention are described in detail below and illustrated in FIGS. 3-6.

However, in the detailed description, only certain exemplary embodiments of the present invention are shown and described, by way of illustration. As those skilled in art will recognize, the invention can be embodied in many different forms and should not be construed as being limited to the embodiments set forth herein.

Diterpene glycosides, including sweet-tasting substances, are found in the stems, seeds and leaves of the *S. rebaudiana* Bertoni plant, being present in the highest concentration in the leaves. The leaves, therefore, are the preferred starting material for recovery of sweet glycosides.

Rebaudioside D purification is developed starting from commercial *Stevia* extract. The content of Rebaudioside D in the extract can vary depending on *Stevia* plant variety or technological scheme of the extract preparation.

*Stevia* extract containing Stevioside—25.40%, Rebaudioside A—59.14%, Rebaudioside C—9.71%, Rebaudioside D—2.03%, Rebaudioside B—0.56%, Rebaudioside E—0.68%, Rebaudioside F—1.02%, Steviolbioside—0.11%, and Dulcoside A—1.35% was used as an exemplary starting material in illustrating the purification of Rebaudioside D.

Figure 3:
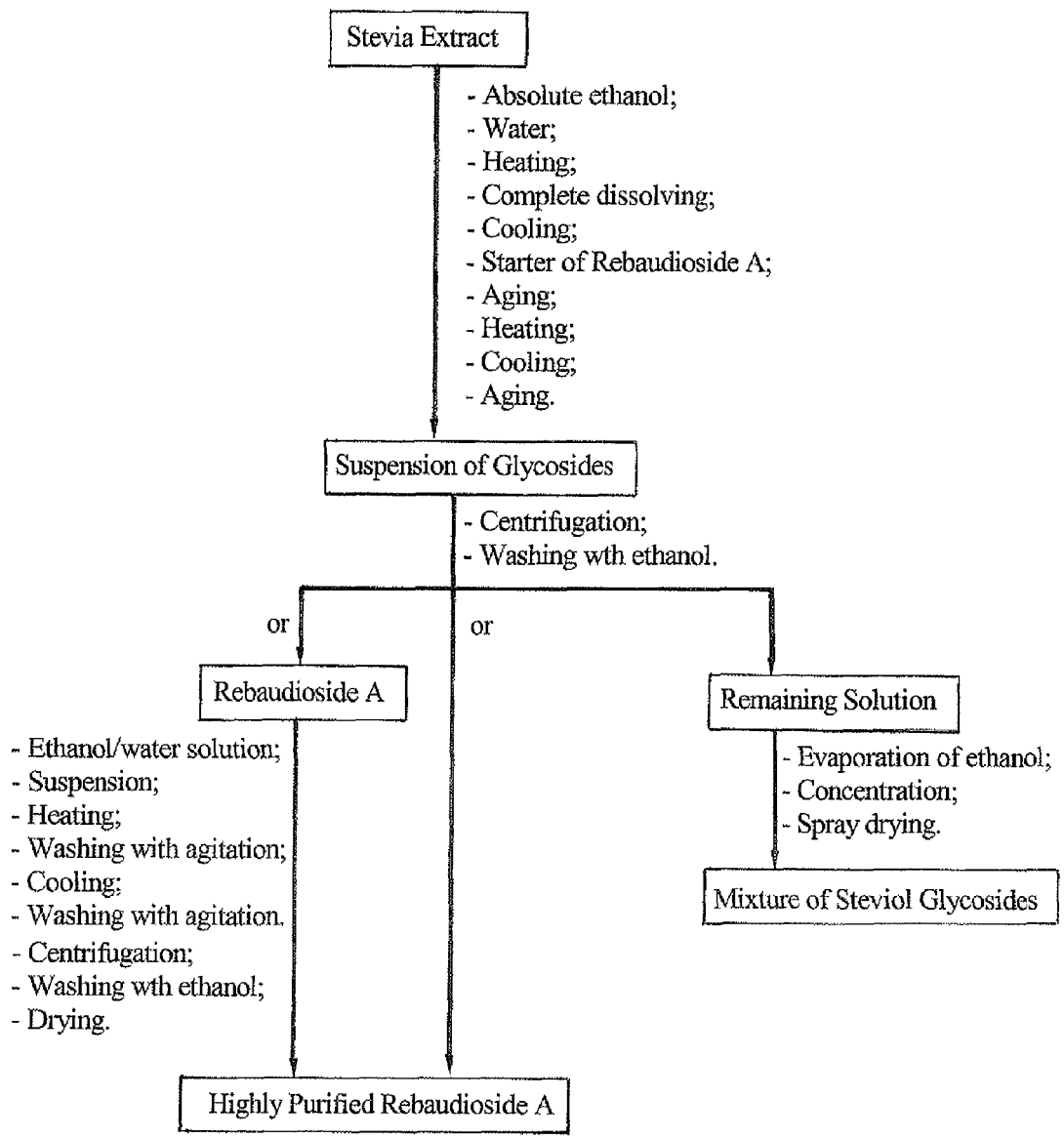
FIG. 3 shows one-stage purification scheme of Rebaudioside A using ethanol-water systems in accordance with one embodiment of the present invention.
Figure 4:
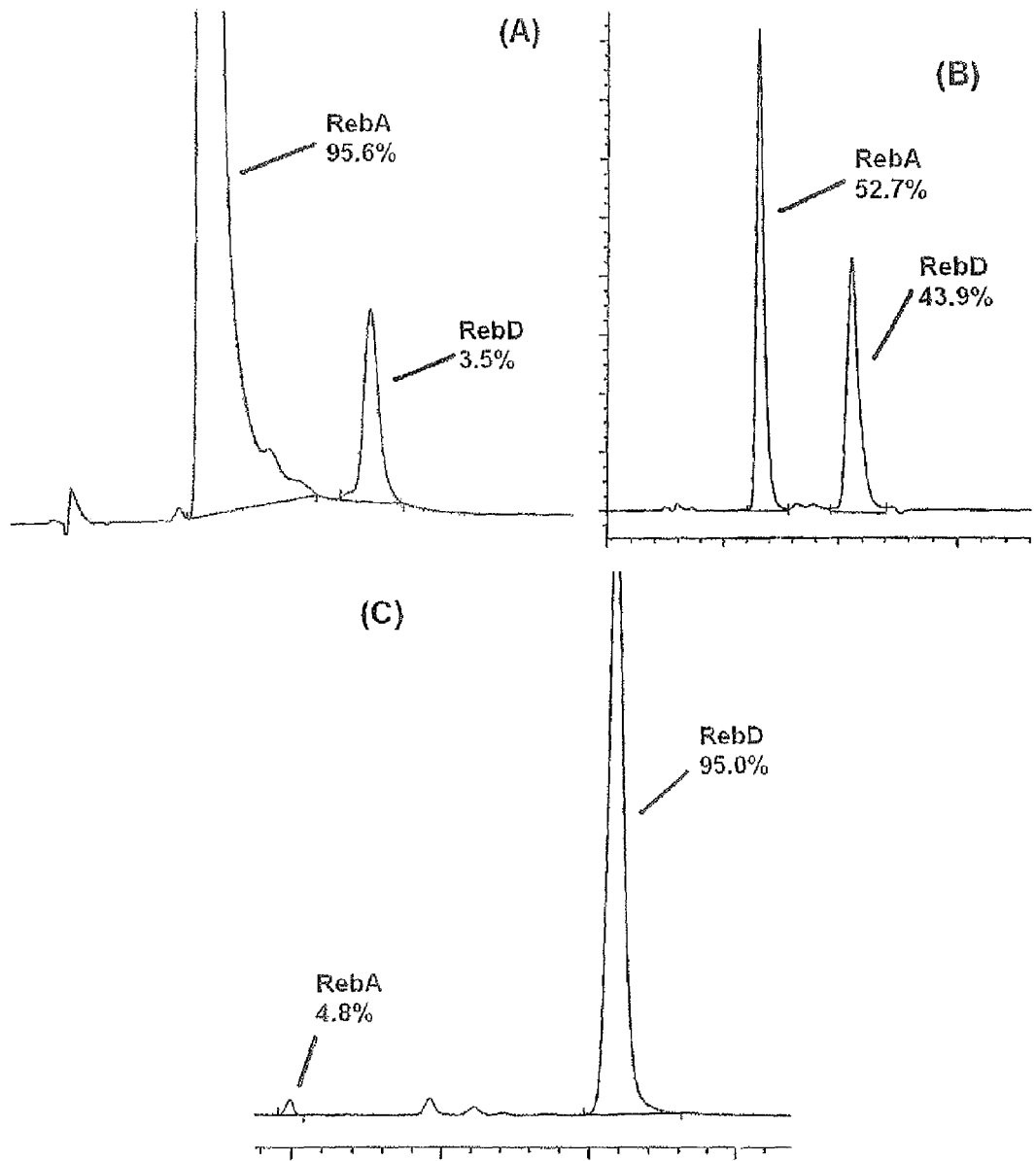
FIG. 4 shows the HPLC charts of Rebaudioside D at various stages of purification.

Now referring to FIG. 3, there is provided a one-stage purification of high purity Rebaudioside A with relatively high Rebaudioside D in accordance with one embodiment of the present invention. *Stevia* extract was dissolved in a first ethanol-water solution at 50-70° C., preferably 55-60° C., for about 10-30 min, preferably 15-20 min, and then at 15-40° C., preferably 20-22° C. for about 18-48 hours, preferably 20-24 hours with agitation. When the temperature reached to 22° C., 1-2% (w/vol.) of highly purified Rebaudioside A was added to the reaction mixture as a starter to initiate crystallization. The proportion of extract and the first ethanol-water solution depended on the content of minor glycosides and was between 1.0:2.5-1.0:10.0, w/v, preferably 1.0:3.0-5.0, w/v.

During this time a first precipitate was formed, which was separated by filtration or centrifugation.

The concentration of ethanol in the first ethanol-water solution is between 75-99%, preferably 82-88%. The content of Rebaudioside A and Rebaudioside D in the first precipitate ranges between 79-99% and 0.8-4.0% respectively.

The purity and yield of Rebaudioside A depended on the ration of extract to ethanol-water solution and concentration of ethanol. The data at various concentrations of ethanol is summarized in the TABLE 3. The extract:methanol ratio was 1:3.0, w/v.

The purification level and output of Rebaudioside A at various volumes of 88% ethanol solution is summarized in the TABLE 4.

TABLE 3

| Ethanol, % | Steviol glycosides, % | | | | | | | | Yield, % |
|---|---|---|---|---|---|---|---|---|---|
| | St | RebA | RebC | RebD | RebB | RebE | RebF | StBio | DulA | |
| 75 | 0.1 | 98.9 | 0.2 | 0.8 | 0 | 0 | 0 | 0 | 0 | 19.2 |
| 78 | 0.1 | 98.6 | 0.2 | 1.0 | 0.1 | 0 | 0 | 0 | 0 | 21.3 |
| 80 | 0.1 | 98.2 | 0.2 | 1.4 | 0.1 | 0 | 0 | 0 | 0 | 23.4 |
| 82 | 0.1 | 97.8 | 0.2 | 1.8 | 0.1 | 0 | 0 | 0 | 0 | 23.7 |
| 85 | 0.1 | 97.6 | 0.2 | 2 | 0.1 | 0 | 0 | 0 | 0 | 24.1 |
| 87 | 0.3 | 96.7 | 0.4 | 2.5 | 0.1 | 0 | 0 | 0 | 0 | 25.6 |
| 88 | 0.4 | 95.6 | 0.3 | 3.5 | 0.1 | 0.1 | 0 | 0 | 0 | 33.0 |
| 89 | 0.8 | 94.2 | 0.7 | 3.5 | 0.2 | 0.1 | 0.2 | 0 | 0.3 | 35.4 |
| 90 | 1.4 | 93.4 | 1.2 | 3.0 | 0.2 | 0.1 | 0.2 | 0.1 | 0.4 | 35.7 |
| 95 | 3.2 | 90.0 | 3.1 | 2.5 | 0.2 | 0.2 | 0.2 | 0.1 | 0.5 | 41.6 |
| 99 | 7.2 | 78.8 | 10.3 | 2.1 | 0.2 | 0.3 | 0.2 | 0.2 | 0.7 | 48.3 |

TABLE 4

| Extract/Ethanol ratio, w/v | Steviol glycosides, % | | | | | | | | | Yield, % |
|---|---|---|---|---|---|---|---|---|---|---|
| | St | RebA | RebC | RebD | RebB | RebE | RebF | StBio | DulA | |
| 1:5.0 | 0.2 | 98.0 | 0.2 | 1.5 | 0 | 0.1 | 0 | 0 | 0 | 26.5 |
| 1:4.0 | 0.2 | 97.5 | 0.2 | 2.0 | 0 | 0.1 | 0 | 0 | 0 | 31.3 |
| 1:3.5 | 0.3 | 96.9 | 0.1 | 2.6 | 0 | 0.1 | 0 | 0 | 0 | 32.4 |
| 1:3.0 | 0.4 | 95.6 | 0.3 | 3.5 | 0.1 | 0.1 | 0 | 0 | 0 | 33.0 |
| 1:2.5 | 2.5 | 91.7 | 1.7 | 3.3 | 0.2 | 0.2 | 0.1 | 0 | 0.3 | 35.6 |
| 1:2.0 | 3.3 | 89.8 | 2.5 | 3.2 | 0.2 | 0.3 | 0.1 | 0.1 | 0.5 | 41.4 |

The Rebaudioside D content increases with the increase of the concentration of ethanol up to 88-90% and the decrease of the ration of ethanol-water solution to extract. At the same time the purity of Rebaudioside A increased with more diluted ethanol solutions and higher ratios of ethanol-water solution to extract.

The yield of the product at this stage for *Stevia* extracts with various contents of Rebaudioside A, after treatment with 1:3 (w/vol.) ratios of 88% ethanol is summarized in the TABLE 5. As it could be expected the yield of the product increases with increase of the content of Rebaudioside A in the initial extract.

TABLE 5

| Rebaudioside A content in initial extract, % | Yield of Rebaudioside A at precipitation stage from initial extract, % |
|---|---|
| 42.0-43.0 | 22.0-25.0 |
| 45.0-46.0 | 22.0-25.0 |
| 50.0-53.0 | 24.0-27.0 |
| 55.0-59.0 | 28.0-31.0 |
| 60.0-62.0 | 32.0-36.0 |

The precipitate was separated by filtration or centrifugation, washed with about two volumes of absolute ethanol and dried. Any type of equipment which allows separation of precipitate from liquid, such as various types of centrifuges or filtration systems can be used in this stage. Different type dryers, such as rotary vacuum dryer, fluid bed dryer, rotary tunnel dryer or plate dryer, are suitable to produce purified steviol glycosides in powder form.

In case if initial extract contains high amount of Rebaudioside B and Rebaudioside D, for Rebaudioside A and later Rebaudioside D purification lower concentrations of ethanol and higher ratio of ethanol-water solution to the extract are preferred to use (TABLE 6; TABLE 7). In this series of experiments the Rebaudioside A content in the initial extract was 48.7%.

The yield of the product with high content of Rebaudioside A and Rebaudioside D can be increased by using ethanol for after-precipitation. For that purpose at the end of crystallization, 0.5-1.0, v/w, preferably 0.5-0.8, v/w, of absolute ethanol to the initial solid, was added to the mixture and the process was continued for another 2-3 hours. The yield and purity of the product from extract with 48.7% of Rebaudioside A content are summarized in TABLE 8.

TABLE 6

| Ethanol, % | Ratio ethanol to solid, v/w | Purity of product at different Rebaudioside B content, % (Rebaudioside D content was 0.4%) | | | |
|---|---|---|---|---|---|
| | | 0% | 0.4% | 0.8% | 1.1% |
| 81.0 | 2.5 | 98.7 | 98.5 | 98.2 | 97.9 |
| | 3.0 | 98.9 | 98.7 | 98.4 | 98.1 |
| | 3.5 | 99.2 | 98.9 | 98.6 | 98.4 |
| 83.0 | 2.5 | 98.1 | 98.2 | 98.0 | 97.7 |
| | 3.0 | 98.5 | 98.4 | 98.2 | 97.9 |
| | 3.5 | 98.8 | 98.6 | 98.4 | 98.2 |
| 85.0 | 2.5 | 97.7 | 97.6 | 97.4 | 97.2 |
| | 3.0 | 98.2 | 97.9 | 97.6 | 97.4 |
| | 3.5 | 98.5 | 98.2 | 97.8 | 97.6 |
| 87.0 | 2.5 | 96.3 | 97.2 | 96.6 | 96.4 |
| | 3.0 | 97.5 | 97.6 | 97.4 | 97.0 |
| | 3.5 | 97.9 | 97.9 | 97.6 | 97.2 |
| 88.0 | 2.5 | 96.1 | 95.9 | 95.5 | 95.1 |
| | 3.0 | 97.3 | 97.1 | 96.4 | 95.8 |
| | 3.5 | 97.7 | 97.5 | 97.2 | 96.8 |
| 90.0 | 2.5 | 94.6 | 94.1 | 92.3 | 90.5 |
| | 3.0 | 96.3 | 95.8 | 92.8 | 91.2 |
| | 3.5 | 97.3 | 96.8 | 93.7 | 91.9 |

TABLE 7

| Ethanol, % | Ratio ethanol to solid, v/w | Purity of product at different content of Rebaudioside D, % (Rebaudioside B content was 0.1%) | | | |
|---|---|---|---|---|---|
| | | 0.5% | 1.2% | 1.7% | 2.6% |
| 81.0 | 2.5 | 98.7 | 98.0 | 97.5 | 97.1 |
| | 3.0 | 98.9 | 98.3 | 98.0 | 97.4 |
| | 3.5 | 99.2 | 98.5 | 98.2 | 97.7 |
| 83.0 | 2.5 | 98.1 | 97.7 | 97.3 | 97.0 |
| | 3.0 | 98.5 | 98.1 | 97.8 | 97.4 |
| | 3.5 | 98.8 | 98.4 | 98.0 | 97.6 |
| 85.0 | 2.5 | 97.7 | 97.5 | 97.1 | 96.8 |
| | 3.0 | 98.2 | 97.8 | 97.6 | 97.1 |
| | 3.5 | 98.5 | 98.1 | 97.8 | 97.2 |
| 87.0 | 2.5 | 96.3 | 96.2 | 95.8 | 94.2 |
| | 3.0 | 97.5 | 97.3 | 96.7 | 96.1 |
| | 3.5 | 97.9 | 97.6 | 97.4 | 96.9 |
| 88.0 | 2.5 | 96.1 | 95.7 | 95.2 | 93.7 |
| | 3.0 | 97.3 | 97.1 | 96.5 | 95.6 |
| | 3.5 | 97.7 | 97.4 | 97.0 | 96.6 |
| 90.0 | 2.5 | 94.6 | 94.2 | 93.5 | 93.0 |
| | 3.0 | 94.8 | 94.8 | 93.9 | 93.3 |
| | 3.5 | 95.7 | 95.4 | 94.4 | 93.5 |

TABLE 8

| Additional ethanol volume, v/w to solids | Yield and purity of RebA at different concentrations of ethanol (ratio of ethanol to extract = 1:3.5, w/v) | | | | | | | |
|---|---|---|---|---|---|---|---|---|
| | 85% | | 86% | | 87% | | 88% | |
| | Yield, % | RebA, % | Yield, % | RebA, % | Yield, % | RebA, % | Yield, % | RebA, % |
| 0 | 29.5 | 98.5 | 30.6 | 98.3 | 32.7 | 97.9 | 33.3 | 97.8 |
| 0.5 | 31.4 | 98.5 | 31.6 | 98.2 | 33.4 | 97.9 | 33.8 | 97.6 |
| 0.6 | 32.3 | 98.2 | 32.7 | 98.2 | 34.3 | 97.8 | 34.7 | 97.6 |
| 0.7 | 33.5 | 97.9 | 33.9 | 97.7 | 35.4 | 97.6 | 35.9 | 97.5 |
| 0.8 | 34.1 | 97.9 | 35.2 | 97.7 | 36.3 | 97.6 | 36.7 | 97.4 |
| 0.9 | 34.3 | 97.8 | 35.4 | 97.6 | 36.7 | 97.5 | 37.4 | 97.4 |
| 1.0 | 34.5 | 97.8 | 35.7 | 97.5 | 36.9 | 97.4 | 37.7 | 97.2 |

To produce high purity Rebaudioside A the process can be carried out at 30-50° C. without cooling stage. Although the purity of Rebaudioside A was higher it resulted in lower yield of the product. The quality of the product increased at higher washing temperatures. The results obtained using 3.5 volumes of 85% ethanol to one part of extract after 24 hours and with and without after-precipitation stage are summarized in TABLE 9.

TABLE 9

| Temperature, °C. | Yield, % | | Content of Rebaudioside A | |
|---|---|---|---|---|
| | Without after-precipitation | With after-precipitation (0.8 vol. EtOH) | Without after-precipitation | With after-precipitation (0.8 vol. EtOH) |
| 22.0 | 29.6 | 33.5 | 98.2 | 98.5 |
| 30.0 | 28.7 | 32.8 | 98.4 | 98.6 |
| 35.0 | 27.5 | 32.2 | 98.7 | 98.9 |
| 40.0 | 27.0 | 31.4 | 98.8 | 99.2 |
| 45.0 | 25.4 | 28.9 | 99.0 | 99.4 |
| 50.0 | 24.3 | 25.6 | 99.2 | 99.5 |

Rebaudioside A, Rebaudioside B and Rebaudioside D contents were 51.3, 0.2% and 0.7%, respectively.

When the content of Rebaudioside A in the final product was less than 97% mainly due to high content of Rebaudioside B and/or Rebaudioside D, the product was additionally washed with aqueous solution of ethanol. For that the Rebaudioside A obtained after the precipitation was suspended in the ethanol-water mixture at room temperature for 30-40 min. After homogeneous suspension was obtained the temperature was increased up to 35-50° C. preferably 38-42° C. and agitated for about 10-20 hours, preferably 12-15 hours, and then at 10-25° C., preferably 20-22° C. for about 3-20 hours, preferably 5-10 hours. The proportion of Rebaudioside A and ethanol was 1.0:2.0-1.0:5.0, w/v, preferably 1.0:2.5-4.0, w/v. The ethanol concentration was between 85-93% preferably 88-90%.

In case if purity of Rebaudioside A was lower than 97% due to high content of Stevioside, the product was washed with absolute ethanol by the same way as it was described above for Rebaudioside B and Rebaudioside D contaminated product. The proportion of Rebaudioside A and ethanol was 1.0:2.0-1.0:5.0, w/v, preferably 1.0:2.5-4.0, w/v.

Figure 5:
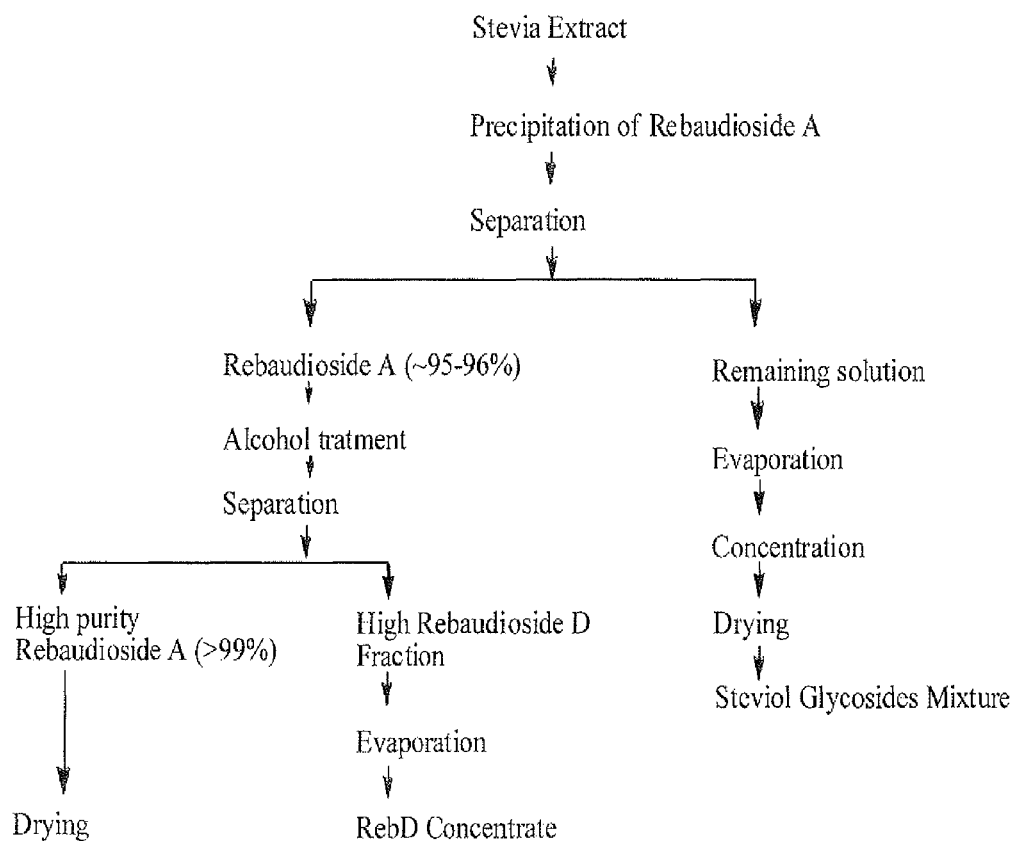
FIG. 5 shows a purification scheme of Rebaudioside D in accordance with one embodiment of the present invention.
Figure 6:
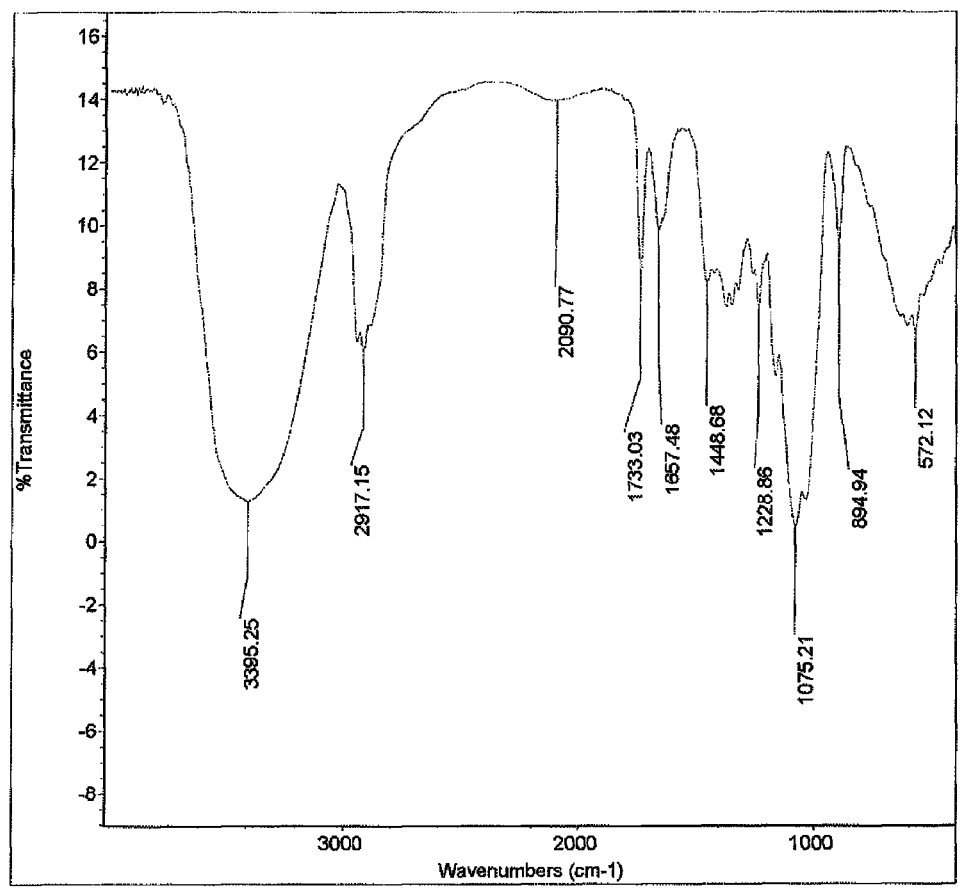
FIG. 6 shows FTIR spectrum of Rebaudioside D.

Now referring to FIG. 5, there is provided a functional flowchart for purification of Rebaudioside A and Rebaudioside D in accordance with one embodiment of the present invention.

Purification of Rebaudioside D from the crystals/precipitates with Rebaudioside A and Rebaudioside D content around 75-80% and 2.0-3.5% respectively, was developed as follows. It is to be noted that the crystals with Rebaudioside A and Rebaudioside D can be obtained from the process as described in connection with FIG. 3.

The precipitate with high content of Rebaudioside A and Rebaudioside D was mixed with a second ethanol-water solution and incubated at 45-65° C. preferably 50-55° C. for 2-6 hours preferably 3-4 hours with agitation. Then, the mixture was cooled down to room temperatures for 1-3 hour preferably 0.5-1.0 hour. The precipitate was separated by filtration.

The preferable ratio of solids to aqueous ethanol solution was 1 to 5, w/v, and the optimum concentration of ethanol was 78%. However ethanol concentration can be in the limits 70-80% and ratio 1:2.5-1.7, w/v.

To facilitate the filtration of high Rebaudioside D precipitate, activated carbon in amount of 0.5-3.0 vol. % preferably 1.0-1.5 vol. % was added to the mixture before filtration. The precipitate was then mixed with 3-5 volumes of 30-50% of methanol. The suspension was maintained with agitation at 45-65° C. preferably 57-62° C. for 1-5 hours preferably 2-3 hours and subjected to filtration. Elution of adsorbed on activated carbon glycosides was carried out with methanol.

Both precipitates obtained without and with carbon application contain 19-22.1% of Rebaudioside D at the optimal conditions (TABLE 10).

TABLE 10

| Ethanol, % | Ratio ethanol to solid, v/w | Purity of RebA, % | Purity of RebD, % |
|---|---|---|---|
| 75.0 | 4.0 | 98.5 | 18.4 |
|  | 5.0 | 99.2 | 18.6 |
|  | 6.0 | 99.4 | 18.6 |
| 77.0 | 4.0 | 98.4 | 18.7 |
|  | 5.0 | 99.1 | 20.1 |
|  | 6.0 | 99.2 | 20.3 |
| 78.0 | 4.0 | 98.4 | 19.2 |
|  | 5.0 | 99.2 | 22.0 |
|  | 6.0 | 99.4 | 22.1 |
| 79.0 | 4.0 | 98.1 | 19.0 |
|  | 5.0 | 98.8 | 19.7 |
|  | 6.0 | 99.0 | 19.8 |
| 80.0 | 4.0 | 98.0 | 17.3 |
|  | 5.0 | 98.4 | 17.9 |
|  | 6.0 | 98.9 | 18.2 |
| 82.0 | 4.0 | 97.7 | 15.2 |
|  | 5.0 | 98.1 | 15.8 |
|  | 6.0 | 98.7 | 16.4 |

In principle the higher the applied volume of methanol the faster can be elution process. The process can be completed in shorter time period when aqueous solution of methanol was used.

The methanol fraction was evaporated to dryness.

When the initial material containing 95.6% of Rebaudioside A and 3.5% Rebaudioside D (FIG. 4a) was mixed with 3.5 volumes of 78.0% of ethanol, the mixture was boiled for 10-15 min and undissolved material was separated by hot filtration, the output of precipitate was in the limits of 6-7.0% with 52-53.0% and 43-45.0% of Rebaudioside A and Rebaudioside D (FIG. 4b) contents, respectively.

For the further purification the precipitate was suspended in 50% ethanol at the ratio of 1:2, w/v and at 30-40° C. preferably 33-37° C., and maintained for 2-15 hour preferably 10-12 hours with agitation. The suspension was filtered and dried. The yield of precipitate with content of about 15-17.0% Rebaudioside A and 80-82% Rebaudioside D was in the range of 42-46.0%. In principle up to five volumes of aqueous ethanol can be applied at this stage. The concentration of ethanol can be in the limits of 10-80% preferably 45-52%.

The precipitate was subjected to similar treatment. The precipitate was separated by filtration, washed with about two volumes of anhydrous methanol and dried. Any type of equipment, which allows separating precipitate from liquid, such as various type centrifuges or filtration systems, can be used in this stage. Different type of dryers, such as rotary vacuum dryer, fluid bed dryer, rotary tunnel dryer or plate dryer are suitable to produce purified Rebaudioside D in powder form.

The purity of Rebaudioside D was around 95-99% content (FIG. 4c). The yield of the product was around 58-60%.

The remaining combined solution after isolation of Rebaudioside D was mixed with small amount of Rebaudioside A as starter and left for crystallization at 20-22° C. for 20-24 hours. Rebaudioside A content in the crystals ranged 97.7-99.4%.

The remaining solution from the first precipitation can be used for isolation of Rebaudioside A or highly purified mixture of steviol glycosides.

High purity Rebaudioside D obtained in this invention has 1129.15 molecular weight, $C_{50}H_{80}O_{28}$ molecular formula and structure presented in the FIG. 2, and is in the form of white and odorless powder. The compound is about 180-200 times sweeter than sugar when compared to 10% sucrose solution. The infrared absorption spectrum is shown in the FIG. 6. Rebaudioside D exhibits a characteristic absorption maximum at around 1730 cm$^{-1}$. Other properties of the pure Rebaudioside D are as follows:

Melting point: 248-249° C.

Specific rotation: $[\lambda]_D^{25}$ −29.5° in 50% ethanol (C=1.0).

Solubility in water is around 0.2% which is increasing with increase in temperature. It precipitates again upon cooling the solution. Highly soluble during chromatographic separation stage and before crystallizing.

Soluble in diluted solutions of methanol, ethanol, n-propanol, and isopropanol.

Insoluble in acetone, benzene, chloroform, and ether.

Rebaudioside D obtained in this invention is heat and pH-stable.

Rebaudioside D obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc. The examples which follow show representative proportions which may be employed.

In addition, Rebaudioside D can be used as a sweetener not only for drinks, foodstuffs, and other products dedicated for human consumption, but also in animal feed and fodder with improved characteristics.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

The sweetener obtained in this invention can be used in dry or liquid forms. It can be added before or after heat treatment of food products. The amount of the sweetener depends on the purpose of usage. It can be added alone or in the combination with other compounds.

In one particular embodiment of this invention Rebaudioside D, as a sweetening compound, may be employed as the sole sweetener, or it may be used together with other naturally occurring high intensity sweeteners.

The phrase "natural high intensity sweeteners", as used herein, refers to any compositions which are found in nature and which have sweetness potency higher than sucrose, fructose, or glucose.

Non-limiting examples of natural high intensity sweeteners include Stevioside, Rebaudioside A, Rebaudioside B, Rebaudioside C, Rebaudioside E, Rebaudioside F, Steviolbioside, Dulcoside A, Rubusoside, mogrosides, brazzein, glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, siamenoside and alike, and combinations thereof.

In another particular embodiment Rebaudioside D as a sweetening compound may be used together with synthetic or artificial high intensity sweeteners.

The phrase "synthetic" or "artificial high intensity sweeteners", as used herein, refers to any compositions which are not found in nature and which have—sweetness potency higher than sucrose, fructose, or glucose.

Non-limiting examples of synthetic or artificial high intensity sweeteners include sucralose, potassium acesulfame, aspartame, alitame, saccharin, neohesperidin dihydrochalcone, cyclamate, neotame, dulcin, suosan, N-[N-[3-(3-hydroxy-4-methoxyphenyl)propyl]-L-α-aspartyl]-L-phenylalanine 1-methyl ester, N-[N-[3-(3-hydroxy-4-methoxyphenyl)-3-methylbutyl]-L-α-aspartyl]-L-phenylalanine 1-methyl ester, N-[N-[3-(3-methoxy-4-hydroxyphenyl)propyl]-L-α-aspartyl]-L-phenylalanine 1-methyl ester, salts thereof, and the like, and combinations thereof.

In one embodiment Rebaudioside D can be used in the combination with natural sweetener suppressors such as gymnemic acid, hodulcin, ziziphin, lactisole, and the like.

In another embodiment Rebaudioside D can be combined with various umami taste enhancers.

In a particular embodiment Rebaudioside D can be formulated with amino acids including, but not limited to, aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, or gamma-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be α-, β-, γ-, δ-, and ε-isomers if appropriate. Combinations of the foregoing amino acids and their corresponding salts (e.g., sodium, potassium, calcium, magnesium salts or other alkali or alkaline earth metal salts thereof, or acid salts) also are suitable additives. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, amino acids encompass both modified and unmodified amino acids. As used herein, modified amino acid also may encompass peptides and polypeptides (e.g., dipeptides, tripeptides, tetrapeptides, and pentapeptides) such as glutathione and L-alanyl-L-glutamine.

In one particular embodiment Rebaudioside D may be formulated with polyamino acid additives include poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, other polymeric forms of amino acids, and salt forms thereof (e.g., magnesium, calcium, potassium, or sodium salts such as L-glutamic acid mono sodium salt). The polyamino acid additives also may be in the D- or L-configuration. Additionally, the polyamino acids may be α-, β-, γ-, δ-, and ε-isomers if appropriate. Combinations of the foregoing polyamino acids and their corresponding salts (e.g., sodium, potassium, calcium, magnesium salts or other alkali or alkaline earth metal salts thereof or acid salts) also are suitable sweet taste improving additives in embodiments of this invention. The polyamino acids described herein also may comprise co-polymers of different amino acids. The polyamino acids may be natural or synthetic. The polyamino acids also may be modified, such that at least one atom has been added, removed, substituted, or combinations thereof (e.g., N-alkyl polyamino acid or N-acyl polyamino acid). As used herein, polyamino acids encompass both modified and unmodified polyamino acids. In accordance with particular embodiments, modified polyamino acids include, but are not limited to polyamino acids of various molecular weights (MW), such as poly-α-lysine with a MW of 1,500, MW of 6,000, MW of 25,200, MW of 63,000, MW of 83,000, or MW of 300,000.

In another particular embodiment Rebaudioside D can be combined with polyols or sugar alcohols. The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols include erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced which do not adversely affect the taste of the sweetener composition, and combinations thereof.

In one particular embodiment Rebaudioside D can be combined with reduced calorie sweeteners such as D-tagatose, L-sugars, L-sorbose, L-arabinose, and others and combinations thereof.

In another particular embodiment Rebaudioside D can be combined with various carbohydrates. The term "carbohydrate" generally refers to aldehyde or ketone compounds substituted with multiple hydroxyl groups, of the general formula $(CH_2O)_n$, wherein "n" is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, substituted, or combinations thereof Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, acyloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Non-limiting examples of carbohydrates in embodiments of this invention include tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiobiose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration. In the formulations any combinations of the compounds can be used.

In a particular embodiment Rebaudioside D may be formulated with sugar acids which is include, but are not limited to, aldonic, uronic, aldaric, alginic, gluconic, glucuronic, glucaric, galactaric, galacturonic, and their salts (e.g., sodium, potassium, calcium, magnesium salts or other physiologically acceptable salts), and combinations thereof.

In a particular embodiment Rebaudioside D can be used in the combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory.

The composition with Rebaudioside D may include a flavoring agent which may be natural or artificial origin. As used herein, unless otherwise indicated, the term "flavor" means any food-grade material that may be added to the present compositions to provide a desired flavor to a foodstuff. The flavors useful in the present invention include, for example, an essential oil, such as an oil derived from a plant or a fruit, peppermint oil, spearmint oil, other mint oils, clove oil, cinnamon oil, oil of wintergreen, bay, thyme, cedar leaf, nutmeg, allspice, sage, mace, and almonds. The flavoring agent may be a plant extract or a fruit essence such as apple, banana, watermelon, pear, peach, grape, strawberry, raspberry, cherry, plum, pineapple, apricot, and mixtures thereof. The flavoring agent may be a citrus flavor, such as an extract, essence, or oil of lemon, lime, orange, tangerine, grapefruit, citron, or kumquat. Flavors useful in the present invention also can include cream, hazelnut, vanilla, chocolate, cinnamon, pecan, lemon, lime, raspberry, peach, mango, vanillin, butter, butterscotch, tea, orange, tangerine, caramel, strawberry, banana, grape, plum, cherry, blueberry, pineapple, elderberry, watermelon, bubblegum, cantaloupe, guava, kiwi, papaya, coconut, mint, spearmint, derivatives, and combinations thereof.

The composition with Rebaudioside D may include an aroma component. As used herein, unless otherwise indicated, the term "aroma component" means any food-grade volatile substance that may be employed to produce a desired scent, for example, when mixed with a foodstuff. Aromas useful in the present invention include, for example, essential oils (citrus oil), expressed oils (orange oil), distilled oils (rose oil), extracts (fruits), anethole (liquorice, anise seed, ouzo, fennel), anisole (anise seed), benzaldehyde (marzipan, almond), benzyl alcohol (marzipan, almond), camphor (cinnamomum camphora), cinnamaldehyde (cinnamon), citral (citronella oil, lemon oil), d-limonene (orange) ethyl butanoate (pineapple), eugenol (clove oil), furaneol (strawberry), furfural (caramel), linalool (coriander, rose wood), menthol (peppermint), methyl butanoate (apple, pineapple), methyl salicylate (oil of wintergreen), neral (orange flowers), nerolin (orange flowers), pentyl butanoate (pear, apricot), pentyl pentanoate (apple, pineapple), sotolon (maple syrup, curry, fennugreek), strawberry ketone (strawberry), substituted pyrazines, e.g., 2-ethoxy-3-isopropylpyrazine; 2-methoxy-3-sec-butylpyrazine; and 2-methoxy-3-methylpyrazine (toasted seeds of fenugreek, cumin, and coriander), thujone (juniper, common sage, Nootka cypress, and wormwood), thymol (camphor-like), trimethylamine (fish), vanillin (vanilla), and combinations thereof Preferred aroma components according to the present invention include, essential oils (citrus oil), expressed oils (orange oil), distilled oils (rose oil), extracts (fruits), benzaldehyde, d-limonene, furfural, menthol, methyl butanoate, pentyl butanoate, salts, derivatives, and combinations thereof.

The compositions with Rebaudioside D can comprise a nucleotide additive for use in embodiments of this invention. They include, but are not limited to, inosine monophosphate, guanosine monophosphate, adenosine monophosphate, cytosine monophosphate, uracil monophosphate, inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, and their alkali or alkaline earth metal salts, and combinations thereof. The nucleotides described herein also may comprise nucleotide-related additives such as nucleosides or nucleic acid bases (e.g., guanine, cytosine, adenine, thymine, uracil).

The compositions with Rebaudioside D can comprise an organic acid additive. Organic acids are compounds which comprises a —COOH moiety. Suitable organic acid additives for use in embodiments of this invention include, but are not limited to, C2-C30 carboxylic acids, substituted hydroxyl C1-C30 carboxylic acids, benzoic acid, substituted benzoic acids (e.g. 2,4-dihydroxybenzoic acid), substituted cinnamic acids, hydroxyacids, substituted hydroxybenzoic acids, substituted cyclohexyl carboxylic acids, tannic acid, lactic acid, tartaric acid, citric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, glucosamine hydrochloride, glucono delta lactone, caffeic acid, bile acids, acetic acid, ascorbic acid, alginic acid, erythorbic acid, polyglutamic acid, and their alkali or alkaline earth metal salt derivatives thereof. In addition, the organic acid additives also may be in either the D- or L-configuration.

The compositions with Rebaudioside D can comprise an organic acid salt additive. They include, but are not limited to, sodium, calcium, potassium, and magnesium salts of all organic acids, such as salts of citric acid, malic acid, tartaric acid, flunaric acid, lactic acid (e.g., sodium lactate), alginic acid (e.g., sodium alginate), ascorbic acid (e.g., sodium ascorbate), benzoic acid (e.g., sodium benzoate or potassium benzoate), and adipic acid. The examples of the sweet taste improving organic acid salt additives described optionally may be substituted with one or more of the following moiety selected from the group consisting of hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phospho, phosphonato, and any other viable functional group, provided the substituted organic acid salt additive functions to improve the sweet taste of the sweetener composition.

The compositions with Rebaudioside D can comprise an inorganic acid additive for use in embodiments of this invention. They include, but are not limited to, phosphoric acid, phosphorous acid, polyphosphoric acid, hydrochloric acid, sulfuric acid, carbonic acid, sodium dihydrogen phosphate, and their corresponding alkali or alkaline earth metal salts thereof (e.g., inositol hexaphosphate Mg/Ca).

The compositions with Rebaudioside D can comprise a bitter compound additive for use in embodiments of this invention, but are not limited to, caffeine, quinine, urea, bitter orange oil, naringin, quassia, and salts thereof.

The compositions with Rebaudioside D can comprise an artificial or natural sweetness enhancers and combinations thereof.

Rebaudioside D formulation may include a polymer additives for use in embodiments of this invention, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polyarginine, polypropylene glycol, polyethylene glycol, poly(ethylene glycol methyl ether), polyaspartic acid, polyglutamic acid, polyethyleneimine, alginic acid, sodium alginate, propylene glycol alginate, sodium hexametaphosphate (SHMP) and its salts, and sodium polyethyleneglycolalginate and other cationic and anionic polymers.

Rebaudioside D formulation may include a protein or protein hydrolyzates additives for use in embodiments of this invention, but are not limited to, bovine serum albumin, whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolyzates, reaction products of protein hydrolyzates, glycoproteins, and/or proteoglyeans containing amino acids (e.g., glycine, alanine, senrme, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolyzates (e.g., porcine collagen hydrolyzates).

Rebaudioside D formulation may include a surfactant additives for use in embodiments of this invention, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Rebaudioside D formulation may include a flavonoid additives for use in embodiments of this invention generally are classified as flavonols, flavones, flavanones, flavan-3-ols, isoflavones, or anthocyanidins. Non-limiting examples of flavonoid additives include catechins (e.g., green tea extracts), polyphenols, rutins, neohesperidin, naringin, neohesperidin dihydrochalcone, and the like.

The formulation may include an alcohol additives for use in embodiments of this invention include, but are not limited to, ethanol.

The formulation may include an astringent compound additives include, but are not limited to, tannic acid, europium chloride ($EuC_3$), gadolinium chloride ($GdCl_3$), terbium chloride ($TbCl_3$), alum, tannic acid, and polyphenols (e.g., tea polyphenols).

The formulation may include a vitamin. Vitamins are organic compounds that the human body needs in small quantities for normal functioning. The body uses vitamins without breaking them down, unlike other nutrients such as carbohydrates and proteins. The vitamins for use in embodiment include, but not limited to, vitamin A (retinol, retinaldehyde, retinoic acid, retinoids, retinal, retinoic acid), vitamin D (vitamins D1-D5; cholecalciferol, lumisterol, ergocalciferol, dihydrotachysterol, 7-dehydrocholesterol), vitamin E (eocopherol, tocotrienol), vitamin K (phylloquinone, naphthoquinone), vitamin B1 (thiamin), vitamin B2 (riboflavin, vitamin G), vitamin 133 (niacin, nicotinic acid, vitamin PP), vitamin B5 (pantothenic acid), vitamin B6 (pyridoxine, pyridoxal, pyridoxamine), vitamin B7 (biotin, vitamin H), vitamin B9 (folic acid, folate, folacin, vitamin M, pteroyl-L-glutamic acid), vitamin B12 (cobalamin, cyanocobalamin), and vitamin C (ascorbic acid).

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methylmethionine. As used herein, the term vitamin includes pseudo-vitamins.

The formulation with Rebaudioside D may include a dietary fiber. Dietary fiber, also known as bulk or roughage, is the portion of food resistant to hydrolysis by human digestive enzymes and generally comprises the indigestible portion of plant materials that moves through the digestive system and stimulates the intestine to peristalsis.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulin, oligosaccharides, fructooligosaccharides, cyclodextrins, chitins, and combinations thereof.

Food sources of dietary fiber include, but are not limited to, grains, legumes, fruits, and vegetables. Grains providing dietary fiber include, but are not limited to, oats, rye, barley, wheat. Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

The formulation containing Rebaudioside D may comprise an antioxidant. Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof In some embodiments, the antioxidant may include vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gulamine, oxalic acid, tocopherol-derived compounds, butylated hydroxyanisole, butylated hydroxyoluene, ethylenediaminetetraacetic acid, tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms theaflavin and its gallate forms, thearubigins, isotlavone phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-.alpha.-lipoic acid, N-acetylcysteine, emblicanin, apple extract, apple skin extract (applephenon), rooibos extract red, rooibos extract, green hawthorn berry extract, red raspberry extract, green coffee antioxidant, aronia extract 20% grape seed extract, cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon hark extract, grape skin extract, bilberry extract, pine bark extract, pycnogenol, elderberry extract, mulberry root extract, wollberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant may comprise a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Some antioxidants belong to the class of phytonutrients called polyphenols (also known as "polyphenolics"), which are a group of chemical substances found in plants, characterized by the presence of more than one phenol group per molecule. A variety of health benefits may derived from polyphenols, including prevention of cancer, heart disease, and chronic inflammatory disease and improved mental strength and physical strength, for example. Suitable polyphenols for embodiments of this invention, include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel. Suitable sources of such antioxidants as proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo. Suitable sources of resveratrol for embodiments of this invention include, but are not limited to, red grapes, peanuts, cranberry, blueberry, bilberry, mulberry, Japanese Itadori tea, and red wine. Suitable sources of isoflavones for embodiments of this invention include, but are not limited to, soy beans, soy products, legumes, alfalfa spouts, chickpeas, peanuts, and red clover. Suitable sources of curcumin for embodiments of this invention include, but are not limited to, turmeric and mustard. Suitable sources of punicalagin and ellagitannin for embodiments of this invention include, but are not limited to, pomegranate, raspberry, strawberry, walnut, and oak-aged red wine. Suitable sources of citrus flavonids, such as hesperidin or naringin, for embodiments of this invention include, but are not limited to, oranges, grapefruits, and citrus juices. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, Echinacea, pycnogenol, and apple peel.

The Rebaudioside D composition may include fatty acids. As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

The composition with Rebaudioside D may include a salt. The term "salt" also refers to complexes that retain the desired chemical activity of the sweet taste improving compositions of the present invention and are safe for human or animal consumption in a generally acceptable range. Alkali metal (for example, sodium or potassium) or alkaline earth metal (for example, calcium or magnesium) salts also can be made. Salts also may include combinations of alkali and alkaline earth metals. Non-limiting examples of such salts are (a) acid addition salts formed with inorganic acids and salts formed with organic acids; (b) base addition salts formed with metal cations such as calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b). Thus, any salt forms which may be derived from the sweet taste improving compositions may be used with the embodiments of the present invention as long as the salts of the sweet taste improving additives do not adversely affect the taste of the sweetener compositions comprising the at least one natural and/or synthetic high-potency sweetener. The salt forms of the additives can be added to the natural and/or synthetic sweetener composition in the same amounts as their acid or base forms.

In particular embodiments, suitable inorganic salts useful in embodiments include, but are not limited to, sodium chloride, potassium chloride, sodium sulfate, potassium citrate, europium chloride ($EuCl_3$), gadolinium chloride ($GdCl_3$), terbium chloride ($TbCl_3$), magnesium sulfate, alum, magnesium chloride, mono- di-, tri-basic sodium or potassium salts of phosphoric acid (e.g., inorganic phosphates), salts of hydrochloric acid (e.g., inorganic chlorides), sodium carbonate, sodium bisulfate, and sodium bicarbonate. Furthermore, in particular embodiments, suitable organic salts useful as sweet taste improving additives include, but are not limited to, choline chloride, alginic acid sodium salt (sodium alginate), glucoheptonic acid sodium salt, gluconic acid sodium salt (sodium gluconate), gluconic acid potassium salt (potassium gluconate), guanidine HCl, glucosamine HCl, amiloride HCl, monosodium glutamate, adenosine monophosphate salt, magnesium gluconate, potassium tartrate (monohydrate), and sodium tartrate (dihydrate).

Rebaudioside D composition obtained according to this invention can be applied as high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, Rebaudioside D composition can be used as a sweetener not only for drinks, foodstuffs, and other products dedicated for human consumption, but also in animal feed and fodder with improved characteristics.

The examples of products where Rebaudioside D compositions can be used as sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

In the detailed description, only certain exemplary embodiments of the present invention are shown and described, by way of illustration. As those skilled in the art will recognize, the invention can be embodied in many different forms and should not be construed as being limited to the embodiments set forth herein.

The sweetener obtained in this invention can be used in dry or liquid forms. I can be added before or after heat treatment of food products. The amount of the sweetener depends on the purpose of usage. It can be added alone or in the combination with other compounds.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions of the present invention can be made by any method known to those skilled in the art that provide homogenous even or homogeneous mixtures of the ingredients. These methods include dry blending, spray drying, agglomeration, wet granulation, compaction, co-crystallization and the like.

In solid form the sweetening composition of the present invention can be provided to consumers in any form suitable for delivery into the comestible to be sweetened, including sachets, packets, hulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

Studies performed showed that the combination of Rebaudioside D with other steviol glycosides, natural high intensity sweeteners and artificial high intensity sweeteners produces a sweetening composition with improved taste profile.

Rebaudioside D and other high intensity sweeteners were combined in various blends where Rebaudioside D contribution in the composition sweetness was from 10% to 90%.

The higher was the content of Rebaudioside D in the mixture the considerable was the improvement effect.

The composition may include various bulking agents, functional ingredients, colorants, flavors.

The following examples illustrate preferred embodiments of the invention for the isolation and purification of Rebaudioside D and related compounds and the use thereof in foodstuffs and pharmaceuticals. It will be understood that the invention is not limited to the materials, proportions, conditions and procedures set forth in the examples, which are only illustrative.

Example 1

Purification of Rebaudioside D

One kg of *Stevia* extract containing *Stevia* extract containing Stevioside—25.40%, Rebaudioside A—59.14%, Rebaudioside C—9.71%, Rebaudioside D—2.03%, Rebaudioside B—0.56%, Rebaudioside E—0.68%, Rebaudioside F—1.02%, Steviolbioside—0.11%, and Dulcoside A—1.35% was dissolved in 3000 ml of 95% ethyl alcohol and maintained at 80° C. for 35 min, and then at 15° C. for 12 hours with agitation. When temperature reached 22° C., 1.0% of highly purified Rebaudioside A was added to the reaction mixture as starter to initiate crystallization.

Precipitate was separated by filtration and washed with about two volumes of 99.5% ethanol.

The yield of crystalline material was 47.1% with content of Stevioside (8.8%), Rebaudioside A (81.7%), Rebaudioside C (5.1%), Rebaudioside D (3.3%), Rebaudioside B (0.1%), Rebaudioside E (0.3%), Rebaudioside F (0.4%), and Dulcoside A (0.3%).

The remaining solution contains Stevioside (40.2%), Rebaudioside A (39.1%), Rebaudioside C (13.8%), Rebaudioside D (0.9%), Rebaudioside B (1.0%), Rebaudioside E (1.0%), Rebaudioside F (1.6%), Steviolbioside (0.2%), and Dulcoside A (2.3%), and can be used for the isolation of Rebaudioside A or highly purified mixture of steviol glycosides.

The precipitate was mixed with 3.5 volumes of 77.7% ethanol and incubated at 50° C. for 3 hours with agitation. Then, the mixture was cooled down to room temperature and the precipitate was separated by filtration. The output of crystals was around 14% and 65.9 g of product was obtained with content of Stevioside (1.4%), Rebaudioside A (72.8%), Rebaudioside C (1.5%), Rebaudioside D (21.4%), Rebaudioside B (0.1%), Rebaudioside E (2.1%), and Rebaudioside F (0.7%).

The content of various glycosides in the filtrate was as follows: Stevioside (10.0%), Rebaudioside A (83.15%), Rebaudioside C (5.69%), Rebaudioside D (0.35%), Rebaudioside B (0.1%), Rebaudioside E (0.01%), Rebaudioside F (0.35%), and Dulcoside A (0.35%).

For further purification of Rebaudioside D the precipitate was suspended in 50% ethanol at 1:2 w/v ratio and maintained for 12 hours at 35° C. with agitation. The suspension was filtered and precipitate was dried. The yield of precipitate was around 23% and it contains Stevioside (0.8%), Rebaudioside A (16.2%), Rebaudioside C (0.7%), Rebaudioside D (81.6%), Rebaudioside E (0.5%), and Rebaudioside F (0.2%). Around 15.2 g of dry material was obtained at this stage.

The content of various glycosides in the resulted filtrate was as follows: Stevioside (1.6%), Rebaudioside A (89.7%), Rebaudioside C (1.7%), Rebaudioside D (3.4%), Rebaudioside B (0.1%), Rebaudioside E (2.6%), and Rebaudioside F (0.8%). It was combined with the filtrate from previous stage.

The precipitate was subjected to similar treatment with 50% ethanol solution to get a product with content of 3.8% Rebaudioside A and 95.7% Rebaudioside D. The product also contains Stevioside, Rebaudioside C and Rebaudioside F 0.1% each as well as 0.2% Rebaudioside E. The yield of this product was around 75% and around 11.4 g of crystals were obtained.

The quantity of filtrate at this stage was around 3.8 g with 39.3% and 53.4% Rebaudioside D and Rebaudioside A respectively.

The obtained Rebaudioside D was dissolved in 2 volumes of 30% methanol and treated with 0.3% of activated carbon at 60° C. for 30 min then subjected to hot filtration. Rebaudioside D spontaneously precipitated after filtration.

The crystals were separated by filtration and dried at 80° C. for 12 hours. The yield of precipitate was around 8.8 g and it contains 98.4% Rebaudioside D on dry base.

The combined filtrate from second and third stage of precipitation was 455.8 g and contains Stevioside (9.1%), Rebaudioside A (83.9%), Rebaudioside C (5.2%), Rebaudioside D (0.7%), Rebaudioside B (0.1%), Rebaudioside F (0.3%), Rebaudioside F (0.4%), and Dulcoside A (0.3%). It was mixed with 1% Rebaudioside A as starter and left for crystallization at 22° C. for 12 hours. The crystals were separated by filtration and washed with about two volumes of ethanol. Rebaudioside A content in the crystals was 98.8% on dry base. The quantity was 273.5 g after drying.

The purity of the Rebaudioside D was determined using HPLC which was performed using a ZORBAX $NH_2$ column (150×4.6 mm, 5 µm) at a temperature of 30° C. The mobile phase comprised a solution of 20% buffer (0.0125% acetic acid and 0.0125% ammonium acetate) and 80% acetonitrile at a flow rate of 1.0 mL/min. 12 µL of each sample was injected in duplicate and the sample was analyzed using a UV detector at 210 nm (4 nm bandwidth) with a reference of 260 nm (100 nm bandwidth). The analysis required a run time ranging from 40 to 60 min.

A buffer solution of 0.0125% acetic acid and 0.0125% ammonium acetate was prepared by dissolving 0.125 g ammonium acetate and 125 µL glacial acetic acid in one liter of water. The retention time of Rebaudioside B was adjusted by varying the ratio of ammonium acetate to acetic acid while maintaining a total of 0.025% of both combined. Increasing the amount of acetic acid decreased the retention time of Rebaudioside B.

A diluent solution was prepared by mixing 500 mL of ethyl alcohol and 500 mL of the buffer solution. Rebaudioside D standards were prepared by diluting 10.0±0.5 mg (recorded to the nearest 0.1 mg) of the Rebaudioside D standard with 4 mL of the diluent solution to make a standard solution of approximately 2500 mg/L. The Rebaudioside D standard solution was injected at 10.8, 11.4, 12.6 and 13.2 μL. The moisture content was measured by Karl Fischer analysis every time a standard was prepared and corrections were made based on the solvent purity according to the certificate of analysis.

Stevioside standards were prepared by diluting 12.5±0.5 mg (recorded to the nearest 0.1 mg) of the stevioside standard with 5 mL of the diluent solution to make a standard solution of approximately 2500 mg/L standard (stock A) (correcting for moisture and purity). The stevioside standard was then diluted using one mL of stock A to ten mL of diluent to produce a 250 mg/L standard (stock B), and stock standards were diluted to final concentrations ranging from 2.5 to 50 mg/L.

Samples of the Rebaudioside D compositions were prepared by diluting 125±2 mg (recorded to the nearest 0.1 mg) of the Rebaudioside D composition with 50 mL of the diluent solution to make a sample solution of approximately 2500 mg/L (correcting for moisture). Individually prepared duplicate samples were injected at 12 μL. If the samples were not analyzed immediately, they were stored without headspace, under nitrogen, and desiccated.

The TABLE 11 provides a guideline for retention times for Rebaudioside D and other steviol glycosides. However, those of ordinary skill in the art should appreciate that the retention times may be modified as needed.

TABLE 11

| Compound | HPLC retention time, min |
| --- | --- |
| Stevioside | 5.4 |
| Rebaudioside A | 7.8 |
| Rebaudioside B | 28.6 |
| Rebaudioside C | 6.0 |
| Rebaudioside D | 15.7 |
| Rebaudioside E | 10.7 |
| Rebaudioside F | 6.4 |
| Steviolbioside | 17.7 |
| Dulcoside A | 4.5 |
| Rubusoside | 3.0 |

Example 2

Low-Calorie Orange Juice Drink 60 g of concentrated orange juice were mixed with 1.1 g of citric acid, 0.24 g of vitamin C, 1.0 g of orange essence, 0.76 g of Rebaudioside D and water, to create a homogeneously dissolved mixture of 1000 mL total amount. Then, the mixture was pasteurized for a period of 20 seconds at about 95° C. in order to prepare an orange juice similar to one made by conventional method. The product had excellent taste profile.

Juices from other fruits, such as apple, lemon, apricot, cherry, pineapple, etc. can be prepared using the same approach.

Example 3

Ice-Cream 1.50 kg of whole milk was heated to 45° C., and 300 grains of milk cream, 100 grams of tagatose, 90 grams of sorbitol, 6 grams of carrageenan as a stabilizer, 3 grams of polysorbate-80 as an emulsifier, and 1.0 gram of Rebaudioside D as in EXAMPLE 10, were added into the milk and stirred until the ingredients completely dissolved. The mixture then was pasteurized at a temperature of 80° C. for 25 seconds. After homogenization the samples were kept at a temperature of 4° C. for 24 hours to complete the aging process. Vanilla flavor (1.0% of the mixture weight) and coloring (0.025% of the mixture weight) are added into the mixture after aging. The mixture was then transferred to ice cream maker to produce ice cream automatically. Samples of produced ice creams were transferred to seal containers and were kept in the freezer at a temperature of −18° C.

The application of sweeteners does not affect the physico-chemical properties of ice cream, as well as the overall attributes of color, smoothness, surface texture, air cell, vanilla aroma intensity, vanilla taste, chalkiness, iciness and melting rate.

Example 4

Yoghurt

In 1 kg of defatted milk, 0.8 grains of high purity Rebaudioside D, prepared according to the invention was dissolved. After pasteurizing at 82° C. for 20 minutes, the milk was cooled to 40° C. A starter in amount of 30 grams was added and the mixture was incubated at 37° C. for 6 hours. Then, the fermented mass was maintained at 10-15° C. for 12 hours.

The product is a low-calorie and low-cariogenic yoghurt, without foreign taste and odor.

Example 5

Ice Lemon Tea

The formula for the beverage was as below:

| Ingredients | Quantity, % |
| --- | --- |
| High purity Rebaudioside D | 0.08 |
| Sodium benzoate | 0.02 |
| Citric acid | 0.27 |
| Ascorbic acid | 0.01 |
| Tea extract | 0.03 |
| Lemon flavor | 0.10 |
| Water | to 100 |

All ingredients were blended and dissolved in the water, and pasteurized. The product possesses excellent taste and flavor.

Example 6

Bread 1 kg of flour, 37.38 grams of fructooligosaccharide syrup, 80 grams of margarine, 20 grams of salt, 20 grains of yeasts, and 0.25 grams of high purity Rebaudioside D, obtained according to the invention were placed into the blender and mixed well. 600 ml of water was poured into the mixture and kneaded sufficiently. At the completion of the kneading process, the dough was shaped and raised for 30 to 45 minutes. The ready dough was placed in oven and baked for 45 minutes. Bread samples had creamy white color, and a smooth texture.

Example 7

Diet Cookie

Flour, 50.0%; margarine, 30.0%; fructose, 10.0%; maltitol, 8.0%; whole milk, 1.0%; salt, 0.2%; baking powder, 0.15%; vanillin, 0.1%; Rebaudioside D, 0.55%; obtained according to this invention were kneaded well in dough-mixing machine. After molding of the dough the cookies were baked at 200° C. for 15 minutes.

The product is a low-calorie diet cookie with excellent taste and appropriate sweetness.

Example 8

Soy Sauce 0.8 g of Rebaudioside D was added to 1000 mL of soy sauce and mixed homogenously. The product had an excellent taste and texture.

Example 9

Tooth Paste

A tooth paste was prepared by kneading a composition comprising of calcium phosphate, 45.0%; carboxymethylcellulose, 1.5%; carrageenan, 0.5%; glycerol, 18.0%; polyoxyethylene sorbitan mono-ester, 2.0%; beta-cyclodextrin, 1.5%; sodium lauroylsarcosinate, 0.2%; flavoring, 1.0%; preservative, 0.1%; Rebaudioside D, obtained according to this invention, 0.2%; and water to 100%, by usual way. The product possesses good foaming and cleaning abilities with appropriate sweetness.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

REFERENCES

Kovylyaeva, G. I., Bakaleinik, G. A., Strobykina, I. Y., Gubskaya, V. I., Sharipova, R. R., Alfonsov, V. A., Kataev, V. E., and Tolstikov, A. G. 2007. Glycosides from *Stevia rebaudiana*. Chemistry of Natural Compounds. V. 43, No. 1, 81-85.

Kohda, H., Kasai, R., Yamazaki, K., Murakami, K., and Tanaka, O. 1976. New sweet diterpene glucosides from *Stevia rebaudiana*. Phytochemistry. V. 15, 981-983.

Starratt, A. N., Kirbi, C. W., Pocs, R., and Brandle J. E. 2002. Rebaudioside F, a diterpene glycoside from *Stevia rebaudiana*. Phytochemistry. V. 59, 367-370.

Kobayashi, M., Horikawa, S., Dergandi, Ueno, J., and Mitsuhashi, H. 1977. Dulcoside A and B, New diterpene glycosides from *Stevia rebaudiana*. Phytochemistry. V/16. 1405-1408.

Shi, R., Xu, M., Shi, Z., Fan, Y., Guo, X., Liu, Y., Wang, C., and He, B. 2002. Synthesis of bifunctional polymeric adsorbent and its application in purification of *Stevia* glycosides. Reactive & Functional Polymers. V. 50. 107-116

Chen, T., Zhang, Y., Liu, X., Shi, Z., Sun, J. and He, B. 1998. Science in China. V. 41. No 4. 436-441.

Chen, T., Zhang, Y., Liu, X., Shi, Z., Sun, J. and He, B. 1999. Science in China. V. 42. No 3. 277-282.

Fuh, W-S., Chiang, B-H. 1990. Purification of steviosides by membrane and ion exchange process. Journal of Food Science. V. 55. No 5. 1454-1457.

Zhang, S. Q., Kumar, A., Kutowy, O. 2000. Membrane-based separation scheme for processing sweetener from *Stevia* leaves. Food Research International. V. 33. 617-620.

Liu, Y., Yiming, C., Lining, W., and J. Jianhua. 1991. Study of stevioside preparation by membrane separation process. Desalination. V. 83. 375-382.

Chen, T., Zhang, Y., Liu, X., and He, B. 1999. Studies on the adsorptive selectivity of the polar resin with carbonyl group on rebaudioside A. Acta Polymeric Scnica. No 4. 398-403.

Moraes, E., Machado., N. R. 2001. Clarification of *Stevia rebaudiana* (Bert.) Bertoni extract by adsorption in modified zeolites. Acta Scientiarum. V.23. No 6. 1375-1380.

Montovaneli, I. C. C., Ferretti, E. C., Simxes, M. R., and C. Silva. 2004. The effect of temperature and flow rate on the clarification of the aqueous *Stevia*-extract in fixed-bed column with zeolites. Brazilian Journal of Chemical Engineering. V. 21. No. 3. 449-458.

Pol, J., Ostra, Karasek, P., Roth, M., Benesova, K., Kotlarikova, P., and J. Caslaysky. 2007. V. 388. 1847-1857.

Bandna, V. J., Singh, B., and V. K. Kaul. 2009. An efficient microwave-assisted extraction process of stevioside and rebaudioside A from *Stevia rebaudiana* (Bertoni). Phytochemical Analysis. V. 20. 240-245.

Teo, C. C., Tan, S. N., Yong, J. W. H., Hew, C. S., and E. S. Ong. 2009. Validation of green-solvent extraction combined with chromatographic chemical fingerprint to evaluate quality of *Stevia rebaudiana* Bertoni. J. Sep. Sci. V. 32. 613-622.

Yoda, S. K., Marques, M. O. M., Ademir J. Petenate, A. J., and M. A. Meireles. 2003. Supercritical fluid extraction from *Stevia rebaudiana* Bertoni using $CO_2$ and $CO_2$+water: extraction kinetics and identification of extracted components. Journal of Food Engineering. V. 57. 125-134.

We claim:

1. A low-calorie fruit juice, comprising:
   a natural sweetener composition comprising Rebaudioside D in the range of 81-96 wt %, Rebaudioside A in the range of 3-16 wt %, Stevioside in the range of 0.1-0.8 wt %, Rebaudioside C in the range of 0.1-0.7 wt %, Rebaudioside F in the range of 0.2-0.5 wt %, Rebaudioside F in the range of 0.1-0.2 wt %;
   fruit juice;
   water; and
   one or more beverage ingredients;
   whereby all components are admixed so as to produce the low-calorie fruit juice.

2. The low-calorie fruit juice of claim 1, wherein the fruit juice is made from one or more fruits selected from the group consisting of orange, apple, lemon, apricot, cherry, strawberry, and pineapple.

3. The low-calorie fruit juice of claim 1, wherein the beverage ingredients include citric acid, vitamin, and orange essence.

4. The low-calorie fruit juice of claim 1, wherein
   the natural sweetener composition is in the range of 0.05-2% (w/v);
   the fruit juice in the range of 5-50% (v/v); and
   the beverage ingredients in the range of 0.1-3%.

5. The low-calorie fruit juice of claim 1, wherein the natural sweetener composition is obtained from *Stevia rebaudiana* Bertoni plant by a method comprising the following steps:

a) providing an extract of *Stevia rebaudiana* Bertoni plant;
b) dissolving the extract in a first aqueous solution of organic solvent to result in a first mixture of steviol glycosides, wherein the organic solvent is selected from the group consisting of methanol, ethanol, 1-propanol, isopropanol, and a mixture thereof, and the organic solvent is 75-99 vol. %;
c) inducing crystallization in the first mixture;
d) filtering the mixture from step (c) to obtain a first precipitate and a first filtrate;
e) dissolving the first precipitate in a second aqueous solution of organic solvent to result in a second mixture, wherein the organic solvent is selected from the group consisting of methanol, ethanol, 1-propanol, isopropanol, and a mixture thereof, and the organic solvent is 70-80 vol. %;
f) inducing crystallization in the second mixture;
g) filtering the mixture from step (f) to obtain a second precipitate and a second filtrate;
h) dissolving the second precipitate in a third aqueous solution of organic solvent to result in a third mixture, wherein the organic solvent is selected from the up consisting of methanol, ethanol, 1-propanol, isopropanol, and a mixture thereof, and the organic solvent is 10-80 vol. %;
i) inducing crystallization in the third mixture; and
j) filtering the mixture from step (i) to obtain a third precipitate and a third filtrate;
whereby the third precipitate is dried to yield the natural sweetener composition.

6. The low-calorie fruit juice of claim 5, wherein the step of (i) inducing crystallization in the third mixture comprises adding Rebaudioside D to promote crystallization.

7. A process for producing the low-caloric fruit juice of claim 1, said process comprising:
   admixing the natural sweetener composition, fruit juice, water, and one or more beverage ingredients; wherein the natural sweetener composition is obtained from *Stevia* extract by a method comprising the following steps:
   a) providing an extract of *Stevia rebaudiana* Bertoni plant;
   b) dissolving the extract in a first aqueous solution of organic solvent to result in a first mixture of steviol glycosides, wherein the organic solvent is selected from the group consisting of methanol, ethanol, 1-propanol, isopropanol, and a mixture thereof, and the organic solvent is 75-99 vol. %;
   c) inducing crystallization in the first mixture;
   d) filtering the mixture from step (c) to obtain a first precipitate and a first filtrate;
   e) dissolving the first precipitate in a second aqueous solution of organic solvent to result in a second mixture, wherein the organic solvent is selected from the group consisting of methanol, ethanol, 1-propanol, isopropanol, and a mixture thereof, and the organic solvent is 70-80 vol. %;
   f) inducing crystallization in the second mixture;
   g) filtering the mixture from step (f) to obtain a second precipitate and a second filtrate;
   h) dissolving the second precipitate in a third aqueous solution of organic solvent to result in a third mixture, wherein the organic solvent is selected from the group consisting of methanol, ethanol, 1-propanol, isopropanol, and a mixture thereof, and the organic solvent is 10-80 vol. %;
   i) inducing crystallization in the third mixture; and
   j) filtering the mixture from step (i) to obtain a third precipitate and a third filtrate;
   whereby the third precipitate is dried to yield the natural sweetener composition;
   whereby all components are admixed so as to produce the low-calorie fruit juice.

8. The process of claim 7, wherein the fruit juice is made from one or more fruits selected from the group consisting of orange, apple, lemon, apricot, cherry, strawberry, and pineapple.

9. The process of claim 7, wherein the beverage ingredients include citric acid, vitamin, and orange essence.

10. The process of claim 7, wherein
    the natural sweetener composition is in the range of 0.05-2% (w/v);
    the fruit juice in the range of 5-50% (v/v); and
    the beverage ingredients in the range of 0.1-3%.

* * * * *